(12) United States Patent
Engelhardt et al.

(10) Patent No.: US 6,986,985 B1
(45) Date of Patent: Jan. 17, 2006

(54) PROCESS FOR PRODUCING MULTIPLE NUCLEIC ACID COPIES IN VIVO USING A PROTEIN-NUCLEIC ACID CONSTRUCT

(75) Inventors: Dean L. Engelhardt, New York, NY (US); Jannis G. Stavrianopoulos, Bay Shore, NY (US); Elazar Rabbani, New York, NY (US); James J. Donegan, Long Beach, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 0 days.

(21) Appl. No.: 09/302,816

(22) Filed: Mar. 3, 1998

Related U.S. Application Data

(63) Continuation of application No. 08/182,621, filed on Jan. 13, 1994, now abandoned.

(51) Int. Cl.
*C12Q 1/68* (2006.01)
*C12N 15/00* (2006.01)
*C12N 15/63* (2006.01)
*C12N 1/20* (2006.01)
*C07H 21/04* (2006.01)

(52) U.S. Cl. ...................... 435/6; 435/91.2; 435/320.1; 435/252.8; 435/174; 435/183; 382/129; 382/133; 382/153; 382/173; 382/286; 382/291; 702/19; 702/22; 935/10; 935/24; 935/72; 536/22.1

(58) Field of Classification Search ............... 435/6, 435/91.1, 91.2, 320.1, 5, 287.2; 436/518; 536/24.3; 935/6
See application file for complete search history.

(56) References Cited

U.S. PATENT DOCUMENTS

| | | |
|---|---|---|
| 4,683,195 A | 7/1987 | Mullis et al. |
| 4,707,440 A | 11/1987 | Stavrianopoulos |
| 4,711,955 A | 12/1987 | Ward et al. |
| 4,957,858 A | 9/1990 | Chu et al. |
| 5,043,272 A | 8/1991 | Hartley |
| 5,118,605 A | 6/1992 | Urdea |
| 5,130,238 A | 7/1992 | Malek |
| 5,241,060 A | 8/1993 | Engelhardt et al. |
| 5,288,609 A | 2/1994 | Engelhardt et al. |
| 5,354,668 A | 10/1994 | Auerback et al. |
| 5,399,491 A | 3/1995 | Kacian et al. |
| 5,455,166 A * | 10/1995 | Walker .................. 435/91.2 |
| 5,516,663 A | 5/1996 | Backman et al. |
| 5,612,212 A | 3/1997 | Gerwitz |
| 5,756,296 A | 5/1998 | Cubicciotti |
| 5,843,723 A | 12/1998 | Dubensky, Jr. et al. |
| 5,871,911 A | 2/1999 | Dahlberg et al. |
| 5,955,351 A * | 9/1999 | Gerdes et al. .......... 435/287.2 |
| 5,958,681 A | 9/1999 | Wetmur et al. |
| 5,965,409 A * | 10/1999 | Pardee et al. .......... 435/91.2 |
| 5,965,409 A * | 10/1999 | Pardee et al. .......... 435/91.2 |

| | | |
|---|---|---|
| 6,183,961 B1 | 2/2001 | Bernstein et al. |
| 6,190,889 B1 | 2/2001 | Jones |

FOREIGN PATENT DOCUMENTS

| | | |
|---|---|---|
| EP | 0178863 | 4/1986 |
| EP | 0320308 | 6/1989 |
| EP | 0435150 | 7/1991 |
| EP | 0439182 | 7/1991 |
| EP | 0450594 | 10/1991 |
| EP | 0492570 | 7/1992 |
| EP | 0497272 | 8/1992 |
| EP | 0500224 | 8/1992 |
| EP | 0543612 | 5/1993 |
| EP | 0128332 | 8/1995 |
| JP | 146299 | 6/1993 |

OTHER PUBLICATIONS

Knorre et al., "Oligonucleotides with highly reactive groups selectively bound by *Escherechia* –*coli* RNA polymerase . . . ", IZV SIB OTD AKAD NAUK SSSR SER BIOL NAUK, vol. 0 (2), pp. 98–104, (English Translation Attached Herewith), 1989.*

Zaichikov et al., "Elongation of oligonucleotides covalently bound to the active center of RNA polymerase", Bioorganicheskaia Khimia, vol. 14 (1), pp. 121–124, (English Translation Attached Herewith), Jan. 1988.*

Romano et al., "Isothermal transcription based assay for the detection of HTLV 1 and HTLV II RNA", United states statutory invention registration, H1,825, Dec. 1999.*

Matthews et al.,"Analytical strategies for the use of DNA probes", Analytical Biochemistry, vol. 169, pp. 1–25, 1988.*

Courey et al.,"Influence of DNA sequence and supercoiling on the process of cruciform formation", Journal of Molecular Biology, vol. 202, pp. 35–43, 1988.*

Barany, F., "Genetic disease detection and DNA amplification using cloned thermostable ligase," Proc. Nat. Acad. Sci USA 88:189–193 (1991).

Fuerst, T.R. et al., "Eukaryotic transient–expression system based on recombinant vaccinia virus that synthesizes bacteriophage T7 RNA polymerase," Proc Nat Acad Sci USA 83: 8122–8126 (1986).

Guatelli, J.C. et al., "Isothermal, in vitro amplification of nucleic acids by a multienzyme reaction modeled after retroviral replication," *Proc Nat Acad Sci. USA* 87: 1874–1878 (1990).

Keller and Manak (*DNA Probes*, MacMillan Publishers Ltd, Great Britain, and Stockton Press (U.S. and Canada, 1989, pp. 225–228).

(Continued)

*Primary Examiner*—W. Gary Jones
*Assistant Examiner*—Sally Sakelaris
(74) *Attorney, Agent, or Firm*—Ronald C. Fedus; Natalie Bogdanos

(57) ABSTRACT

This invention provides in vitro processes for producing copies of specific nucleic acids using protein-nucleic acid constructs which are part of conjugates which are introduced into cells. Illustrative of the elements useful in these constructs for producing copies of specific nucleic acids are promoters, sequences coding for proteins or providing templates for transcription, and RNA polymerases.

18 Claims, 27 Drawing Sheets

OTHER PUBLICATIONS

Karkas, J.D. et al., "Action of DNA Polymerase I of *Escherichia coli* with DNA–RNA Hybrids as Templates," Proc Nat Acad Sci U.S.A. 69(2): 398–402 (1972).

Kievits, T., et al. "NASBA™ isothermal enzymatic in vitro nucleic acid amplification optimized for the diagnosis of HIV–1 infection," *J. Virol. Methods 35*: 273–286 (1991).

Kwoh, D.Y. et al., "Transcription–based amplification system and detection of amplified human immunodeficiency virus type 1 with a bead–based sandwich hybridization format," *Proc Nat Acad Sci. USA., 86*: 1173–1177 (1989).

Landegren, U., et al., "Ligase–Mediated Gene Detection Technique," Science 241: 1077 (1988).

Lizardi et al., "Exponential amplification of recombinant RNA hybridization probes," *Biotechnology 6*: 1197–1202 (1988).

U.S. Appl. No. 09/565,667, filed Oct. 5, 1992, Stavrianopoulos et al.

Mullis and Faloona, "Specific Synthesis of DNA in Vitro via a Polymerase–Catalyzed Chain Reaction," *Methods in Enzymology 155*: 335–351 (1987).

Saiki, et al., "Enzymatic Amplification of β–Globin Genomic Sequences and Restriction Site Analysis for Diagnosis of Sickle Cell Anemia," *Science 230*: 1350–1354 (1985).

Walker, G.T. et al., "Isothermal in vitro amplification of DNA by a restriction enzyme/DNA polymerase system," *Proc. Natl Acad Sci USA 89*: 392–396 (1992).

Walker, G.T. et al., "Strand displacement amplification—an isothermal, in vitro DNA amplification technique," *Nuc Acids Res. 20*: 1691–1696 (1992).

Wetmur, J.G. and Davidson, N., "Kinetics of Renaturation of DNA," *J. Mol. Biol. 31*: 349–370 (1968).

Wu, D. and Wallace, R.B. "The Ligation Amplification Reaction (LAR)—Amplification of Specific DNA Sequences Using Sequential Rounds of Template–Dependent Ligation," *Genomics 4*: 560–569 (1989).

Knorre et al. "Oligonucleotides with Highly Reactive Groups Selectively Bound by *E. Coli* RNA Polymerase: Identification of the Enzyme Subunits Interacting with Them and The Competitive Inhibition of Transcription," *IZV SIB OTD ADAD NAUK SSR SER BIOL NAUK 0(2)*: 98–104 (1989).

Meric et al., "Rous Sarcoma Virus Nucleic Acid–binding Protein p12 is Necessary for Viral 70S RNA Dimer Formation and Packaging," *Journal of Virology, 60(2)*: 450–459 (1986).

Ostrander et al. "Template Supercoiling by a Chimera of Yeast GAL4 Protein and Phage T7 RNA Polymerase," *Science: 249*: 1261–1265 (1990).

Promega Catalog, p. 150, Figure 4G.

Watson et al. *In Molecular Biology of the Gene*, Benjamin/Cummings, Publishing, Ch 10 (1987).

Courey et al. "Influence of DNA Sequence and Supercoiling on the Process of Cruciform Formation," Journal of Molecular Biology 202:35–43 (1988).

Matthews et al., "Analytical Strategies for the Use of DNA Probes," Analytical Biochemistry 169: 1–25 (1988).

Romano et al., U.S. Statutory Invention Registration No. H1,825, published Dec. 7, 1999.

Zaichikov et al., "Study of the Elongation of Oligonucleotides Covalently Fixed at the Active Center of RNA–Polymerase," *Biorganicheskaia Khimia 14(1)*:121–124 (1988).

* cited by examiner

Construct Forms Comprising at Least One
Single-Stranded Region

Functional Forms of the Construct

Three Constructs with an RNA Polymerase Covalently Attached to a Transcribing Cassette Product Sequence | T7 Promotor | First RNA Promotor (e.g. Pol III) | T7 RNA Pol'ase First RNA Promotor (e.g. Pol III) | T7 Promotor | T7 RNA Pol'ase | Product Sequence First RNA Promotor (e.g. Pol III) | T7 Promotor (weak) | T7 RNA Pol'ase | T7 Promotor (strong) | Product Sequence Three Constructs with Promoters for Endogenous RNA Polymers

FIG. 5A

M13mp18 Nucleic Acid Sequence

M13mp18. Seq    Length: 7250

```
   1    AATGCTACTA  CTATTAGTAG  AATTGATGCC  ACCTTTTCAG  CTCGCGCCCC
  51    AAATGAAAAT  ATAGCTAAAC  AGGTTATTGA  CCATTTGCGA  AATGTATCTA
 101    ATGGTCAAAC  TAAATCTACT  CGTTCGCAGA  ATTGGGAATC  AACTGTTACA
 151    TGGAATGAAA  CTTCCAGACA  CCGTACTTTA  GTTGCATATT  TAAAACATGT
 201    TGAGCTACAG  CACCAGATTC  AGCAATTAAG  CTCTAAGCCA  TCCGCAAAAA
 251    TGACCTCTTA  TCAAAAGGAG  CAATTAAAGG  TACTCTCTAA  TCCTGACCTG
 301    TTGGAGTTTG  CTTCCGGTCT  GGTTCGCTTT  GAAGCTCGAA  TTAAAACGCG
 351    ATATTTGAAG  TCTTTCGGGC  TTCCTCTTAA  TCTTTTTGAT  GCAATCCGCT
 401    TTGCTTCTGA  CTATAATAGT  CAGGGTAAAG  ACCTGATTTT  TGATTTATGG
 451    TCATTCTCGT  TTTCTGAACT  GTTTAAAGCA  TTTGAGGGGG  ATTCAATGAA
 501    TATTTATGAC  GATTCCCCAG  TATTGGACGC  TATCCAGTCT  AAACATTTTA
 551    CTATTACCCC  CTCTGGCAAA  ACTTCTTTTG  CAAAAGCCTC  TCGCTATTTT
 601    GGTTTTTATC  GTCGTCTGGT  AAACGAGGGT  TATGATAGTG  TTGCTCTTAC
 651    TATGCCTCGT  AATTCCTTTT  GGCGTTATGT  ATCTGCATTA  GTTGAATGTG
 701    GTATTCCTAA  ATCTCAACTG  ATGAATCTTT  CTACCTGTAA  TAATGTTGTT
 751    CCGTTAGTTC  GTTTTATTAA  CGTAGATTTT  TCTTCCCAAC  GTCCTGACTG
 801    GTATAATGAG  CCAGTTCTTA  AAATCGCATA  AGGTAATTCA  CAATGATTAA
 851    AGTTGAAATT  AAACCATCTC  AAGCCCAATT  TACTACTCGT  TCTGGTGTTC
 901    TCGTCAGGGC  AAGCTTATT   CACTGAATGA  GCAGCTTTGT  TACGTTGATT
 951    TGGGTAATGA  ATATCCGGTT  CTTGTCGAAG  ATTACTCTTG  ATGAAGGTCA
1001    GCCAGCCTAT  GCGCCTGGTC  TGTAGACCGT  TCATCTGTCC  TCTTTCAAAG
1051    TTGGTCAGTT  CGGTTCCCTT  ATGATTGACC  GTCTGCGCCT  CGTTCCGGCT
1101    AAGTAACATG  GAGCAGGTCG  CGGATTTCGA  CACAATTTAT  CAGGCGATGA
1151    TACAAATCTC  CGTTGTACCTT TGTTTCGCGC  TTGGTATAAT  CGCTGGGGGT
1201    CAAAGATGAG  TGTTTTAGTG  TATTCTTTCG  CCTCTTTCGT  TTTAGGTTGG
```

FIG. 5B

M13mp18 NUCLEIC ACID SEQUENCE

| | | | | | |
|---|---|---|---|---|---|
| 1251 | TGCCTTCGTA | GTGGCATTAC | GTATTTTACC | CGTTTAATGG | AAACTTCCTC |
| 1301 | ATGAAAAAGT | CTTTAGTCCT | CAAAGCCTCT | GTAGCCGTTG | CTACCCTCGT |
| 1351 | TCCGATGCTG | TCTTTCGCTG | CTGAGGGTCA | CGATCCCGCA | AAAGCGGCCT |
| 1401 | TTAACTCCCT | GCAAGCCTCA | GCGACCGAAT | ATATCGGTTA | TGCGTGGGCG |
| 1451 | ATGGTTGTTG | TCATTGTCGG | CGCAACTATC | GGTATCAAGC | TGTTTAAGAA |
| 1501 | ATTCACCTCG | AAAGCAAGCT | GATAAACCGA | TACAATTAAA | GGCTCCTTTT |
| 1551 | GGAGCCTTTT | TTTTTGGAGA | TTTTCAACGT | GAAAAAATTA | TTATTCGCAA |
| 1601 | TTCCTTTAGT | TGTTCCTTTC | TATTCTCACT | CCGCTGAAAC | TGTTGAAAGT |
| 1651 | TGTTTAGCAA | AACCCCATAC | AGAAAATTCA | TTTACTAACG | TCTGGAAAGA |
| 1701 | CGACAAAACT | TTAGATCGTT | ACGCTAACTA | TGAGGGTTGT | CTGTGGAATG |
| 1751 | CTACAGGCGT | TCTAGTTTGT | ACTGGTGACG | AAACTCAGTG | TTACGGTACA |
| 1801 | TGGGTTCCTA | TTGGGCTTGC | TATCCCTGAA | AATGAGGGTG | GTGGCTCTGA |
| 1851 | GGGTGGCGGT | TCTGAGGGTG | GCGGTTCTGA | GGGTGGCGGT | ACTAAACCTC |
| 1901 | CTGAGTACGG | TGATACACCT | ATTCCGGGCT | ATACTTATAT | CAACCCTCTC |
| 1951 | GACGGCACTT | ATCCGCCTGG | TACTGAGCAA | AACCCGCTA | ATCCTAATCC |
| 2001 | TTCTCTTGAG | GAGTCTCAGC | CTCTTAATAC | TTTCATGTTT | CAGAATAATA |
| 2051 | GGTTCCGAAA | TAGGCAGGGG | GCATTAACTG | TTTATACGGC | CACTGTTACT |
| 2101 | CAAGGCACTG | ACCCCGTTAA | AACTTATTAC | CAGTACACTC | CTGTATCATC |
| 2151 | AAAAGCCATG | TATGACGCTT | ACTGGAACGG | TAAATTCAGA | GACTGCGCTT |
| 2201 | CAAGGCACTG | ACCCCGTTAA | AACTTATTAC | CAGTACACTC | CTGTATCATC |
| 2251 | AAAAGCCATG | TGCCTCAACC | TCCTGTCAAT | GCTGGCGGCG | GCTCTGGTGG |
| 2301 | TCCATTCTGG | CTTTAATCAA | GATCCATTCG | TTTGTGAATA | TCAAGGCCAA |
| 2351 | TCGTCTGACC | TGCCTCAACC | TCCTGTCAAT | GCTGGCGGCG | GCTCTGGTGG |
| 2401 | TGGTTCTGGT | GGCGGCTCTG | AGGGTGGTGG | CTCTGAGGGT | GGCGGTTCTG |
| 2451 | AGGGTGGCGG | CTCTGAGGGA | GGCGGTTCCG | GTGGTGGCTC | TGGTTCCGGT |
| 2501 | GATTTTGATT | ATGAAAAGAT | GGCAAACGCT | AATAAGGGGG | CTATGACCGA |
| 2551 | AAATGCCCAT | GAAAACGCGC | TACAGTCTGA | CGCTAAAGGC | AAACTTGATT |

FIG. 5C

M13mp18 Nucleic Acid Sequence

| | | | | | |
|---|---|---|---|---|---|
| 2601 | CTGTCGCTAC | TGATTACGGT | GCTGCTATCG | ATGGTTTCAT | TGGTGACGTT |
| 2651 | TCCGGCCTTG | CTAATGGTAA | TGGTGCTACT | GGTGATTTTG | CTGGCTCTAA |
| 2701 | TTCCCAAATG | GCTCAAGTCG | GTGACGGTGA | TAATTCACCT | TTAATGAATA |
| 2751 | ATTTCCGTCA | ATATTTACCT | TCCCTCCCTC | AATCGGTTGA | ATGTCGCCCT |
| 2801 | TTTGTCTTTA | GCGCTGGTAA | ACCATATGAA | TTTTCTATTG | ATTGTGACAA |
| 2851 | AATAAACTTA | TTCCGTGGTG | TCTTTGCGTT | TCTTTTATAT | GTTGCCACCT |
| 2901 | TTATGTATGT | ATTTTCTACG | TTTGCTAACA | TACTGCGTAA | TAAGGAGTCT |
| 2951 | TTATCATGCC | AGTTCTTTTG | GGTATTCCGT | TATTATTGCG | TTTCCTCGGT |
| 3001 | TTCCTTCTGG | TAACTTTGTT | CGGCTATCTG | CTTACTTTTC | TTAAAAAGGG |
| 3051 | CTTCGGTAAG | ATAGCTATTG | CTATTTCATT | GTTTCTTGCT | CTTATTATTG |
| 3101 | GGCTTAACTC | AATTCTTGTG | GGTTATCTCT | CTGATATTAG | CGCTCAATTA |
| 3151 | CCCTCTGACT | TTGTTCAGGG | TGTTCAGTTA | ATTCTCCCGT | CTAATGCGCT |
| 3201 | TCCCTGTTTT | TATGTTATTC | TCTCTGTAAA | GGCTGCTATT | TTCATTTTTG |
| 3251 | ACGTTAAACA | AAAAATCGTT | TCTTATTTGG | ATTGGGATAA | ATAATATGGC |
| 3301 | TGTTTATTTT | GTAACTGGCA | AATTAGGCTC | TGGAAAGACG | CTCGTTAGCG |
| 3351 | TTGGTAAGAT | TCAGGATAAA | ATTGTAGCTG | GGTGCAAAAT | AGCAACTAAT |
| 3401 | CTTGATTTAA | GGCTTCAAAA | GCTCCCGCAA | GTCGGGAGGT | TCGCTAAAAC |
| 3451 | GCCTCGCGTT | CTTAGAATAC | CGGATAAGCC | TTCTATATCT | GATTTGCTTG |
| 3501 | CTATTGGGCG | CGGTAATGAT | TCCTACGAATG | AAAATAAAAA | CGGCTTGCTT |
| 3551 | GTTCTCGATG | AGTGCGGTAC | TTGGTTTAAT | ACCCGTTCTT | GGAATGATAA |
| 3601 | GGAAAGACAG | CCGATTATTG | ATTGGTTTCT | ACTGCTCGT | AAATTAGGAT |
| 3651 | GGGATATTAT | TTTTCTTGTT | CAGGACTTAT | CTATTGTTGA | TAAACAGGCG |
| 3701 | CGTTCTGCAT | TAGCTGAACA | TGTTGTTTAT | TGTCGTCGTC | TGGACAGAAT |
| 3751 | TACTTTACCT | TTTGTCGGTA | CTTTATATTC | TCTTATTACT | GGCTCGAAAA |
| 3801 | TGCCTCTGCC | TAAATTACAT | GTTGGCGTTG | TTAAATATGG | CGATTCTCAA |
| 3851 | TTAAGCCCTA | CTGTTGAGCG | TTGGCTTTAT | ACTGGTAAGA | ATTTGTATAA |
| 3901 | CGCATATGAT | ACTAAACAGG | CTTTTTCTAG | TAATTATGAT | TCCGGTGTTT |

FIG. 5D

M13mp18 Nucleic Acid Sequence

| | | | | | |
|---|---|---|---|---|---|
| 3951 | ATTCTTATTT | AACGCCTTAT | TTATCACACG | GTCGGTATTT | CAAACCATTA |
| 4001 | AATTTAGGTC | AGAAGATGAA | ATTAACTAAA | ATAATATTGA | AAAAGTTTTC |
| 4051 | TCGCGTTCTT | TGTCTTGCGA | TTGGATTTGC | ATCAGCATTT | ACATATAGTT |
| 4101 | ATATAACCCA | ACCTAAGCCG | GAGGTTAAAA | AGGTAGTCTC | TCAGACCTAT |
| 4151 | GATTTTGATA | AATTCACTAT | TGACTCTTCT | GAGCGTCTTA | ATCTAAGCTA |
| 4201 | TCGCTATGTT | TTCAAGGATT | CTAAGGGAAA | ATTAATTAAT | AGCGACGATT |
| 4251 | TACAGAAGCA | AGGTTATTCA | CTCACATATA | TTGATTTATG | TACTGTTTCC |
| 4301 | ATTAAAAAAG | GTAATTCAAA | TGAAATTGTT | AAATGTAATT | AATTTTGTTT |
| 4351 | TCTTGATGTT | TGTTTCATCA | TCTTCTTTTG | CTCAGGTAAT | TGAAATGAAT |
| 4401 | AATTCGCCTC | TGCGCGATTT | TGTAACTTGG | TATTCAAAGC | AATCAGGCGA |
| 4451 | AATCCGTTAT | GTTTCTCCCG | ATGTAAAAGG | TACTGTTACT | GTATATTCAT |
| 4501 | CTGACGTTAA | ACCTGAAAAT | CTACGCAATT | TCTTTATTTC | TGTTTTACGT |
| 4551 | GCTAATAATT | TTGATAATGGT | TGGTTCAATT | CCTTCCATAA | TTCAGAAGTA |
| 4601 | TAATCCAAAC | AATCAGGATT | ATATTGATGA | ATTGCCATCA | TCTGATAATC |
| 4651 | AGGAATATGA | TGATAATTCC | GCTCCTTCTG | GTGGTTTCTT | TGTTCCGCAA |
| 4701 | AATGATAATG | TTACTCAAAC | TTTTAAAATT | AATAACGTTC | GGGCAAAGGA |
| 4751 | TTTAATACGA | GTTGTCGAAT | TGTTTGTAAA | GTCTAATACT | TCTAAATCCT |
| 4801 | CAAATGTATT | ATCTATTGAC | GGCTCTAATC | TATTAGTTGT | TAGTGCTCCT |
| 4851 | AAAGATATTT | TAGATAACCT | TCCTCAATTC | CTTTCTACTG | TTGATTTGCC |
| 4901 | AACTGACCAG | ATATTGATTG | AGGGTTTGAT | ATTTGAGGTT | CAGCAAGGTG |
| 4951 | ATGCTTTAGA | TTTTTCATTT | GCTGCTGGCT | CTCAGCGTGG | CACTGTTGCA |
| 5001 | GGCGGTGTTA | ATACTGACCG | CCTCACCTCT | GTTTTATCTT | CTGCTGGTGG |
| 5051 | TTCGTTCGGT | ATTTTTAATG | GCGATGTTTT | AGGGCTATCA | GTTCGCGCAT |
| 5101 | TAAAGACTAA | TAGCCATTCA | AAAATATTGT | CTGTGCCACG | TATTCTTACG |
| 5151 | CTTTCAGGTC | AGAAGGGTTC | TATCTCTGTT | GGCCAGAATG | TCCCTTTTAT |
| 5201 | TAAAGACTAA | TAGCCATTCA | AAAATATTGT | CTGTGCCACG | TATTCTTACG |
| 5251 | CGATTGAGCC | TCAAAATGTA | GGTATTTCCA | TGAGCGTTTT | TCCTGTTGCA |

FIG. 5E

M13mp18 Nucleic Acid Sequence

| | | | | | |
|---|---|---|---|---|---|
| 5301 | ATGGCTGGCG | GTAATATTGT | TCTGGATATT | ACCAGCAAGG | CCGATAGTTT |
| 5351 | GAGTTCTCT | ACTCAGGCAA | GTGATGTTAT | TACTAATCAA | AGAAGTATTG |
| 5401 | CTACAACGGT | TAATTTGCGT | GATGGACAGA | CTCTTTTACT | CGGTGGCCTC |
| 5451 | ACTGATTATA | AAAACACTTC | TCAAGATTCT | GGCGTACCGT | TCCTGTCTAA |
| 5501 | AATCCCTTTA | ATCGGCCTCC | TGTTTAGCTC | CCGCTCTGAT | TCCAACGAGG |
| 5551 | AAAGCACGTT | ATACGTGCTC | GTCAAAGCAA | CCATAGTACG | CGCCCTGTAG |
| 5601 | CGGCGCATTA | AGCGCGGCGG | GTGTGGTGGT | TACGCGCAGC | GTGACCGCTA |
| 5651 | CACTTGCCAG | CGCCCTAGCG | CCCGCTCCTT | TCGCTTTCTT | CCCTTCCTTT |
| 5701 | CTCGCCACGT | TCGCCGGCTT | TCCCCGTCAA | GCTCTAAATC | GGGGGCTCCC |
| 5751 | TTTAGGGTTC | CGATTTAGTG | CTTTACGGCA | CCTCGACCCC | AAAAAACTTG |
| 5801 | ATTTGGGTGA | TGGTTCACGT | AGTGGGCCAT | CGCCCTGATA | GACGGTTTTT |
| 5851 | CGCCCTTTGA | CGTTGGAGTC | CACGTTCTTT | AATAGTGGAC | TCTTGTTCCA |
| 5901 | AACTGGAACA | ACACTCAACC | CTATCTCGGG | CTATTCTTTT | GATTTATAAG |
| 5951 | GGATTTTGCC | GATTTCGGAA | CCACCATCAA | ACAGGATTTT | CGCCTGCTGG |
| 6001 | GGCAAACCAG | CGTGGACCGC | TTGCTGCAAC | TCTCTCAGGG | CCAGGCGGTG |
| 6051 | AAGGGCAATC | AGCTGTTGCC | CGTCTCGCTG | GTGAAAAGAA | AAACCACCCT |
| 6101 | GGCGCCCAAT | ACGCAAACCG | CCTCTCCCCG | CGCGTTGGCC | GATTCATTAA |
| 6151 | TGCAGCTGGC | ACGACAGGTT | TCCCGACTGG | AAAGCGGGCA | GTGAGCGCAA |
| 6201 | CGCAATTAAT | GTGAGTTAGC | TCACTCATTA | GGCACCCCAG | GCTTTACACT |
| 6251 | TTATGCTTCC | GGCTCGTATG | TTGTGTGGAA | TTGTGAGCGG | ATAACAATTT |
| 6301 | CACACAGGAA | ACAGCTATGA | CCATGATTAC | GAATTCGAGC | TCGGTACCCG |
| 6351 | GCGATCCTCT | AGAGTCGACC | TGCAGGCATG | CAAGCTTGGC | ACTGGCCGTC |
| 6401 | GTTTTACAAC | GTCGTGACTG | GGAAAACCCT | GGCGTTACCC | AACTTAATCG |
| 6451 | CCTTGCAGCA | CAATCCCCTT | TCGCCAGCTG | GCGTAATAGC | GAAGAGGCCC |
| 6501 | GCACCGATCG | CCCTTCCCAA | CAGTTGCGCA | GCCTGAATGG | CGAATGGCGC |
| 6551 | TTTGCCTGGT | TTCCGGCACC | AGAAGCGGTG | CCGGAAAGCT | GGCTGGAGTG |
| 6601 | CGATCTTCCT | GAGGCCGATA | CGGTCGTCGT | CCCCTCAAAC | TGGCAGATGC |

FIG. 5F

M13mp18 Nucleic Acid Sequence

| | | | | | |
|---|---|---|---|---|---|
| 6651 | ACGGTTACGA | TGCGCCCATC | TACACCAACG | TAACCTATCC | CATTACGGTC |
| 6701 | AATCCGCCGT | TTGTTCCCAC | GGAGAATCCG | ACGGGTTGTT | ACTCGCTCAC |
| 6751 | ATTTAATGTT | GATGAAAGCT | GGCTACAGGA | AGGCCAGACG | CGAATTATTT |
| 6801 | TTGATGGCGT | TCCTATTGGT | TAAAAAATGA | GCTGATTTAA | CAAAAATTTA |
| 6851 | ACGCGAATTT | TAACAAAATA | TTAACGTTTA | CAATTTAAAT | ATTTGCTTAT |
| 6901 | ACAATCTTCC | TGTTTTTGGG | GCTTTTCTGA | TTATCAACCG | GGGTACATAT |
| 6951 | GATTGACATG | CTAGTTTTAC | GATTACCGTT | CATCGATTCT | CTTGTTTGCT |
| 7001 | CCAGACTCTC | AGGCAATGAC | CTGATAGCCT | TTGTAGATCT | CTCAAAAATA |
| 7151 | GCTACCCTCT | CCGGCATGAA | TTTATCAGCT | AGAACGGTTG | AATATCATAT |
| 7101 | TGATGGTGAT | TTGACTGTCT | CCGGCCTTTC | TCACCCTTTT | GAATCTTTAC |
| 7151 | CTACACATTA | CTCAGGCATT | GCATTTAAAA | TATATGAGGG | TTCTAAAAAT |
| 7201 | TTTTATCCTT | GCGTTGAAAT | AAAGGCTTCT | CCCGCAAAAG | TATTACAGGG |
| 7251 | TCATAATGTT | TTTGGTACAA | CCGATTTAGC | TTTATGCTCT | GAGGCTTTAT |

FIG. 6

Primers for Nucleic Acid Production Derived from M13mp18 Nucleic Acid Sequence

| POSITION | 5'     *     3' | COMPLEMENTARY TO M13 POSITION | |
|---|---|---|---|
| 645 | AGCAACACTATCATA | 631 | M13/1 |
| 615 | ACGACGATAAAAACC | 601 | M13/2 |
| 585 | TTTTGCAAAAGAAGT | 571 | M13/3 |
| 555 | AATAGTAAAATGTTT | 541 | M13/4 |
| 525 | CAATACTGCGGAATG | 511 | M13/5 |
| 495 | TGAAAACGAGAATGA | 481 | M13/6 |
| 465 | AGAAAACGAGAATGA | 451 | M13/7 |
| 435 | CAGGTCTTTACCCTG | 421 | M13/8 |
| 405 | AGGAAAGCGGATTGC | 391 | M13/9 |
| 375 | AGGAAGCCCGAAAGA | 361 | M13/10 |

| POSITION | 5'   *   *   3' | COMPLEMENTARY TO SS PHAGE DNA POSITION | |
|---|---|---|---|
| 351 | ATATTTGAAGTCTTT | 366 | M13/11 |
| 371 | TCTTTTTGATGCAAT | 386 | M13/12 |
| 391 | CTATAATACTCAGGG | 406 | M13/13 |
| 411 | TGATTTATGGTCATT | 426 | M13/14 |
| 431 | GTTTAAAGCATTTGA | 446 | M13/15 |
| 451 | TATTTATGACGATTC | 466 | M13/16 |
| 471 | TATCCAGTCTAAACA | 486 | M13/17 |
| 491 | CTCTGGCAAAACTTC | 506 | M13/18 |
| 511 | TCGCTATTTTGGTTT | 526 | M13/19 |
| 531 | AAACGAGGGTTATGA | 546 | M13/20 |

Appropriate M13mp18 Restriction Sites

Lane 1: from calf thymus + Taq digested mp18 amplification reaction
Lane 2: from Taq digested mp18 amplification reaction
Lane 3: from calf thymus amplification reaction
Lane 4: ØX174 Hinf1 size marker Lane 1: no template
Lane 2: mp18 template, phosphate buffer
Lane 3: Mspl/pBR322 size marker
Lane 4: mp18 template, MOPS buffer

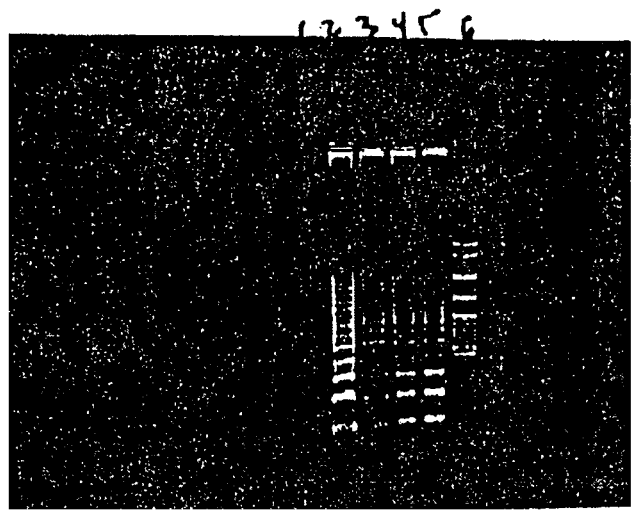
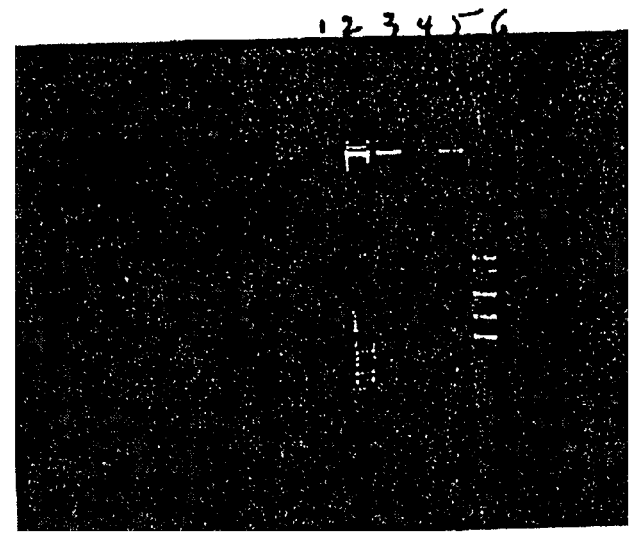
Top= (+) Template
Bottom= (−) Template
Lane 1: phosphate buffer
Lane 2: MES
Lane 3: MOPS
Lane 4: DMAB
Lane 5: DMG
Lane 6: pBR322/MspI size marker
FIG. 10

Lane 1: DMAB buffer, no template
Lane 2: DMAB buffer, mp18 template
Lane 3: DMG buffer, no template
Lane 4: DMG buffer, mp18 template
Lane 5: no reaction
Lane 6: 200 ng Taq I digested mp18 size marker/positive control First Time Interval    Second Time Interval Agarose Gel Analysis Lane 1: Lambda Hind III marker
Lane 2: Amp/Untreated
Lane 3: Amp/Kinased
Lane 4: Amp/Kinased/Ligated
Lane 5: PCR/Untreated
Lane 6: PCR/Kinased
Lane 7: PCR/Kinased/Ligated
Lane 8: ϕX174/Hinf1 marker Lane 1: Primers alone
Lane 2: Primers + taq digested M13 DNA
Lane 3: Molecular weight markers
Lane 4: Primers + RNA
Lane 5: Primers alone
Lane 6: M13 digested DNA
Buffer was dimethyl amino glycine, pH 8.6

Lane 1: Primers alone
Lane 2: Primers + taq digested M13 DNA
Lane 3: Molecular weight markers
Lane 4: Primers + RNA
Lane 5: Primers alone
Lane 6: M13 digested DNA
Buffer was dimethyl amino glycine, pH 8.6 pIBI 31-BH5-2

```
                fmet AUG of Lac z                    {T7 Promotor region....
LAC PROMOTOR..ATG ACC ATG ATT ACG CCA GAT ATC AAA TTA ATA CGA CTC ACT ATA oligo 50-mer      3'- tac t*aa t*gc ggt* ct*a t*ag t*Vt aat* tat* gct* gag t*ga t*at* c-5'
                                        10 base insert T7 RNA Start  {<< << T3 Promotor Region }
              IGGG CTC ICCT TTA GTG ACG GTT AAT
              ...>> >>}  <<- T3 Start Signal
``` pIBI 31 BSII/HCV

```
                fmet AUG of Lac z                    {T3 Promotor region ->>} T3 RNA Start
LAC PROMOTOR..ATG ACC ATG ATT ACG CCA AGC TCG AAA TTA ACC CTC ACT AAA /GGG
oligo 50-mer  3'- tac    t*aa t*ac t*aa t*gc ggt* t*V--10 base insert--...............

{<<- T7 Promotor Region }
MULTIPLE CLONING SITE + 390 BASE INSERT CTA /TAG TGA GTC CGT ATT AAT....
                              <<- T7 Start Signal
                              5'-ct*a  t*ag t*ga gt*c gt*a tt*a at*.........
```

FIG. 18

Cloning Site in Production Constructs

PROCESS FOR PRODUCING MULTIPLE NUCLEIC ACID COPIES IN VIVO USING A PROTEIN-NUCLEIC ACID CONSTRUCT

CROSS-REFERENCE TO OTHER RELATED APPLICATIONS

This application is a continuation of U.S. application Ser. No. 08/182,621 filed on Jan. 13, 1994, abandoned.

FIELD OF THE INVENTION

This invention relates to the field of in vitro and in vivo production of nucleic acid production and to nucleic constructs and protein-nucleic acid conjugates for use in such production.

All patents, patent publications, scientific articles, and videocassettes cited or identified in this application are hereby incorporated by reference in their entirety in order to describe more fully the sfate of the art to which the present invention pertains.

BACKGROUND OF THE INVENTION

Current methodology cited heretofore in the literature relating to amplification of a specific target nucleic acid sequence in vitro essentially involve 2 distinct elements:

1. repeated strand separation or displacement or a specific "Intermediate" structure such as a promoter sequence linked to the primer or introduction an assymetric restrictrion site not originally present in the nucleic acid target; followed by 2. production of nucleic acid on the separated strand or from an "intermediate" structure.

Separation can be accomplished thermally or by enzymatic means. Following this separation, production is accomplished enzymatically using the separated strands as templates.

Of the established amplification procedures, Polymerase Chain Reaction (PCR) is the most widely used. This procedure relies on thermal strand separation, or reverse transcription of RNA strands followed by thermal dissociation. At least one primer per strand is used and in each cycle only one copy per separated strand is produced. This procedure is complicated by the requirement for cycling equipment, high reaction temperatures and specific thermostable enzymes. (Saiki, et al., Science 230:1350–1354 (1985); Mullis and Faloona, Methods in Enzymology 155: 335–351 (1987); U.S. Pat. Nos. 4,683,195 and 4,883,202).

Other processes, such as the Ligase Chain Reaction (LCR) (Backman. K., European Patent Application Publication No. 0 320 308; Landegren, U., et al. Science 241 1077 (1988); Wu, D. and Wallace, R. B. Genomics 4 560 (1989); Barany, F. Proc. Nat. Acad. Sci USA 88:189 (1991)), and Repair Chain Ligase Reaction (RLCR) or Gap Ligase Chain Reaction (GLCR) (Backman, K. et al. (1991) European Patent Application Publication No. 0 439 182 A; Segev, D. (1991) European Patent Application Publication No. 0 450 594) also use repeated thermal separation of the strands and each cycle produces only one ligated product. These procedures are more complicated than PCR because they require the use of an additional thermostable enzyme such as a ligase.

More complicated procedures are the Nucleic Acid Sequence Based Amplification (NASBA) and Self Sustained Sequence Reaction (3SR) amplification procedures. (Kwoh, D. Y. et al., Proc Nat Acad Sci., USA., 86:1173–1177 (1989); Guatelli, J. C. et al., 1990 Proc Nat Acad Sci., USA 87:1874–1878 (1990) and the Nucleic Acids Sequence Based Amplification (NASBA) (Kievits, T., et al J. Virol. Methods 35:273–286 (1991); and Malek, L. T., U.S. Pat. No. 5,130,238). These procedures rely on the formation of a new "intermediate" structure and an array of different enzymes, such as reverse transcriptase, ribonuclease H, T7 RNA polymerase or other promotor dependant RNA polymerases and they are further disadvantaged by the simultaneous presence of ribo- and deoxyribonucleotide tripohsphates precursors.

For the intermediate construct formation, the primer must contain the promoter for the DNA dependent RNA polymerase. The process is further complicated because the primer is, by itself, a template for the RNA polymerase, due to its single-stranded nature.

The last of the major amplification procedures is Strand Displacement Amplification (SDA) (Walker, G. T. and Schram, J. L., European Patent Application Publication No. 0 500 224 A2; Walker, G. T. et al. European Patent Application No. 0 543 612 A2; Walker, G. T., European Patent Application Publication No. 0 497 272 A1; Walker, G. T. et al., Proc Natl Acad Sci USA 89:392–396 (1992); and Walker, G. T. et al., Nuc Acids Res. 20:1691–1696 (1992)). The intermediate structure of this procedure is formed by the introduction of an artificial sequence not present in the specific target nucleic acid and which is required for the assymetric recognition site of the restriction enzyme. Again this procedure involves more than one enzyme and the use of thio nucleotide triphosphate precursors in order to produce this assymetric site necessary for the production step of this amplification scheme.

The random priming amplification procedure (Hartley, J. L., U.S. Pat. No. 5,043,272) does not relate to specific target nucleic acid amplification.

Probe amplification systems have been disclosed which rely on either the amplification of the probe nucleic acid or the probe signal following hybridization between probe and target. As an example of probe amplification is the Q-Beta Replicase System (Qβ) developed by Lizardi and Kramer and their colleagues. Qβ amplification is based upon the RNA-dependent RNA polymerase derived from the bacteriophage Qβ. This enzyme can synthesize large quantities of product strand from a small amount of template strand, roughly on the order of $10^6$ to $10^9$ (million to billion) increases. The Qβ replicase system and its replicatable RNA probes are described by Lizardi et al., "Exponential amplification of recombinant RNA hybridization probes," *Biotechnology* 6:1197–1202 (1988); Chu et al., U.S. Pat. No. 4,957,858, and well as by Keller and Manak (*DNA Probes*, MacMillan Publishers Ltd, Great Britain, and Stockton Press (U.S. and Canada, 1989, pages 225–228). As discussed in the latter, the Oβ replicase system is disadvantaged by non-specific amplification, that is, the amplification of non-hybridized probe material, which contributes to high backgrounds and low signal-to-noise ratios. Such attendent background significantly reduces probe amplification from its potential of a billion-fold amplification to something on the order of $10^4$ (10,000 fold). In addition, the Q beta amplification procedure is a signal amplification—and not a target amplification.

In vivo

Literature covering the introduction of genes or antisense nucleic acids into a cell or organism is very extensive (Larrick, J. W. and Burck, K. Gene Therapy Elsevier Science Publishing Co., Inc. New York (1991); Murray, J. A. H. ed Antisense RNA and DNA, Wiley-Liss, Inc., New York (1992)). The biological function of these vectors generally requires inclusion of at least one host polymerase promoter.

The present invention as it relates to in vitro and in vivo production of nucleic acids is based on novel processes, constructs and conjugates which overcome the complexity and limitations of the above-mentioned documents.

SUMMARY OF THE INVENTION

The present invention provides an in vitro process for producing more than one copy of a specific nucleic acid in which the process is independent of any requirement for the introduction of an intermediate structure for the production of the specific nucelc acid. The process comprises three steps, including (a) providing a nucleic acid sample containing or suspected of containing the sequence of the specific nucleic acid; (b) contacting the sample with a three component reaction mixture; and (c) allowing the mixture to react under isostatic conditions of temperature, buffer and ionic strength, thereby producing more than one copy of the specific nucleic acid. The reaction mixture comprises: (i) nucleic acid precursors, (ii) one or more specific nucleic acid primers each of which is complementary to a distinct sequence of the specific nucleic acid, and (iii) an effective amount of a nucleic acid producing catalyst.

In another aspect, the present invention provides an in vitro process for producing more than one copy of a specific nucleic acid in which the products are substantially free of any primer-coded sequences. Such a process comprises the following steps, including (a) providing a nucleic acid sample containing or suspected of containing the sequence of the specific nucleic acid; (b) contacting the sample with a three component mixture (the mixture comprising (i) nucleic acid precursors, (ii) one or more specific polynucleotide primers comprising at least one ribonucleic acid segment each of which primer is substantially complementary to a distinct sequence of the specific nucleic acid, and (iii) an effective amount of a nucleic acid producing catalyst); and (c) allowing the mixture to react under isostatic conditions of temperature, buffer and ionic strength, thereby producing at least one copy of the specific nucleic acid; and (d) removing substantially or all primer-coded sequences from the product produced in step (c). By removing such sequences, a primer binding site is regenerated, thereby allowing a new priming event to occur and producing more than one copy of the specific nucleic acid.

The present invention also provides an in vitro process for producing more than one copy of a specific nucleic acid in which the products are substantially tree of any primer-coded sequences. In the steps of this process, said process comprising a nucleic acid sample containing or suspected of containing the sequence of the specific nucleic acid is provided, and contacted with a reaction mixture. The mixture comprises (i) unmodified nucleic acid precursors, (ii) one or more specific chemically-modified primers each of which primer is substantially complementary to a distinct sequence of said specific nucleic acid, and (iii) an affective amount of a nucleic acid producing catalyst. The mixture thus contacted is allowed to react under isostatic conditions of temperature, buffer and ionic strength, thereby producing at least one copy of the specific nucleic acid. In a further step, substantially or all primer-coded sequences from the product produced in the reacting step is removed to regenerate a primer binding site. The regeneration of a primer binding site thereby allows a new priming event to occur and the production of more than one copy of said specific nucleic acid.

An additional provision of the present invention is an in vitro process for producing more than one copy of a specific nucleic acid in which the products are substantially free of any primer-coded sequences. In this instance, the process comprises the steps of: (a) providing a nucleic acid sample containing or suspected of containing the sequence of the specific nucleic acid; and (b) contacting the sample with a reaction mixture (the mixture comprising (i) unmodified nucleic acid precursors, (ii) one or more specific unmodified primers comprising at least segment each of which primer comprises at least one non-complementary sequence to a distinct sequence of the specific nucleic acid, such that upon hybridization to the specific nucleic acid, at least one loop structure is formed, and (iii) an effective amount of a nucleic acid producing catalyst). The mixture so formed is allowed to react in step (c) under isostatic conditions of temperature, buffer and ionic strength, thereby producing at least one copy of the specific nucleic acid, which step is followed by (d) removing substantially or all primer-coded sequences from the product produced in step (c) to regenerate a primer binding site. The regeneration of a primer binding site thereby allows a new priming event to occur and the production of more than one copy of said specific nucleic acid.

Another embodiment of the present invention concerns a promoter-independent non-naturally occurring nucleic acid construct which when present in a cell produces a nucleic acid without the use of any gene product coded by the construct.

In yet another embodiment, the present invention provides a conjugate comprising a protein-nucleic acid construct in which the nucleic acid construct does not code for said protein, and which conjugate produces a nucleic acid when present in a cell.

The present invention also has significant in vivo applications. In one such application, an in vivo process is provided for producing a specific nucleic acid. The in vivo process comprises the steps of (a) providing a conjugate comprising a protein-nucleic acid construct, the conjugate being capable of producing a nucleic acid when present in a cell; and (b) introducing such a conjugate into a cell, thereby producing the specific nucleic acid.

Another significant aspect of the present invention relates to a construct comprising a host promoter located on the construct such that the host transcribes a sequence in the construct coding for a different RNA polymerase, which after translation is capable of recognizing its cognate promoter and transcribing from a DNA sequence of interest from the construct with the cognate promoter oriented such that it does not promote transcription from the construct of the different RNA polymerase.

BRIEF DESCRIPTION OF THE DRAWINGS

FIG. 5(A–F) is a nucleic acid sequence for M13mp18.

FIG. 6 shows the sequence and the positions of the primers derived from M13mp18 which were employed in the present invention for nucleic acid production.

FIG. 10 is an agarose gel with a lane legend that illustrates the results of a qualitative analysis of the effects observed in Example 9 of various buffers on the amplification reaction in accordance with the present invention.

FIG. 18 depicts the polylinker sequences of the IBI 31 plasmid (pIBI 31-BH5-2) and the BlueScript II plasmid construct (pBSII//HCV).

DETAILED DESCRIPTION OF THE INVENTION

Figure 1A:
FIG. 1(A–F) depicts various nucleic acid construct forms contemplated by the invention in which at least one single-stranded region are located therein.

The present invention describes novel methods and constructs for production of multiple copies of specific nucleic acid sequences in vitro and in vivo.

One aspect of this invention represents an in vitro process for the production of more than one copy of nucleic acid from specific target nucleic acid (either DNA or RNA) sequences utilizing a biological catalyst, e.g., a DNA polymerase, primer oligonucleotides complementary to sequences (primer sites) in the target nucleic acid. The production process can proceed in the presence of a large excess of other nucleic acids and does not require thermal cycling or the introduction of specific intermediate constructs such as promoters or assymetric restriction sites, etc.

More particularly, this invention provides an in vitro process for producing more than one copy of a specific nucleic acid, the process being independent of a requirement for the introduction of an intermediate structure for the production of any such specific nucleic acid. The in vitro production process comprises the steps of: (a) providing a nucleic acid sample containing or suspected of containing the sequence of the specific nucleic acid; (b) contacting the sample with a three component mixture; and (c) allowing the thus-contacted mixture to react under isostatic conditions of temperature, buffer and ionic strength, thereby producing more than one copy of the specific nucleic acid. The three component mixture just alluded will generally comprise (i) nucleic acid precursors, (ii) one or more specific nucleic acid primers each of which is complementary to a distinct sequence of the specific nucleic acid, and (iii) an effective amount of a nucleic acid producing catalyst. In other aspects, the specific nucleic acid may be single-stranded or double-stranded, and may take the form of deoxyribonucleic acid, ribonucleic acid, a DNA.RNA hybrid or a polymer capable of acting as a template for a nucleic acid polymerizing catalyst.

In addition, the specific nucleic acid can be in solution in which case the above-described in vitro process may further comprise the step of treating the specific nucleic acid with a blunt-end promoting restriction enzyme. Further, isolation or purification procedures can be employed to enrich the specific nucleic acid. Such procedures are well-known in the art, and may be carried out on the specific nucleic acid prior to the contacting step (b) or the reacting step (c). One means of isolation or purification of a nucleic acid involves its immobilization, for example, by sandwich hybridization (Ranki et al., 1983), or sandwich capture. Particularly significant in the latter methodology is the disclosure of Engelhardt and Rabbani, U.S. patent application Ser. No. 07/968,706, filed on Oct. 30, 1992, entitled "Capture Sandwich Hybridization Method and Composition," now allowed, that was published as European Patent Application Publication No. 0 159 719 A2 on Oct. 30, 1985. The contents of the foregoing U.S. patent application is incorporated herein by reference.

The target nucleic can be be present in a variety of sources. For purposes of disease diagnosis these would include blood, pus, feces, urine, sputum, synovial fluid, cerebral spinal fluid, cells, tissues, and other sources. The production process can be performed on target nucleic that is present in samples which are free of interfering substances, or the production process can be performed on target nucleic acid separated from the sample. The nucleic acid can be in solution or bound to a solid support. While the replication process can be carried out in the presence of nonrelevant nucleic acids, certain applications may require prior separation of the target sequences. Methods such as sandwich hybridization or sandwich capture referenced above can then be applied to immobilize target sequences. In such instances where sandwich hybridization or sandwich capture is carried out, the above-described in vitro process may further comprise the step of releasing the captured nucleic acid, e.g., by means of a restriction enzyme.

As described above, the target sequence need not be limited to a double-stranded DNA molecule. Target molecules could also be single stranded DNA or RNA. For example, replication of a single-stranded target DNA could proceed using primers complementary to both the single-stranded DNA target and to the produced complementary sequence. Following the initial synthesis of the complementary sequence DNA, production from this strand would begin. RNA can serve as the template using a DNA polymerase I, e.g., Klenow, which can reverse transcribe under conditions that have been described (Karkas, J. D. et al., Proc Nat Acad Sci U.S.A 69:398–402 (1972)).

In case the target nucleic acid is double stranded, a restriction digest or sonication, partial endonuclease treatment or denaturation could be employed for the preparation of the target nucleic acid before the onset of amplification.

An aspect of this invention concerns its use in determining whether a specific target nucleic acid was derived from a living or a deceased organism. To make such a determination, one could in parallel amplify and detect the presence of a specific target DNA or a specific target RNA associated with the genomic makeup of the organism; and thereafter amplify and detect the presence of a specific RNA target associated to the biological function (living function) of the organism which does not survive if the organism is deceased.

The nucleic acid precursors contemplated for use in the present invention are by and large well-known to those skilled in the art. Such precursors may take the form of nucleoside triphosphates and nucleoside triphosphate analogs, or even combinations thereof. More particularly, such nucleoside triphosphates are selected from deoxyadenosine 5'-triphosphate, deoxyguanosine 5'-triphosphate, deoxythymidine 5'-triphosphate, deoxycytidine 5'-triphosphate, adenosine 5'-triphosphate, guanosine 5'-triphosphate, uridine 5'-triphosphate and cytidine 5'-triphosphate, or a combination of any of the foregoing. Such nucleoside triphosphates are widely available commercially, or they may be synthesized by techniques or equipment using commercially available precursors.

In the case where the nucleic acid precursors comprise nucleoside triphosphate analogs, these are also widely available from a number of commercial sources, or they may be manufactured using known techniques. Such nucleoside triphosphate analogs can be in the form of naturally occurring or synthetic analogs, or both.

It should not go unrecognized or even unappreciated that the foregoing nucleoside triphosphate and nucleoside triphosphate analogs can be unmodified or modified, the latter involving modifications to the sugar, phosphate or base moieties. For examples of such modifications, see Ward et al., U.S. Pat. No. 4,711,955; Engelhardt et al., U.S. Pat. No. 5,241,060; Stavrianopoulos, U.S. Pat. No. 4,707,440; and Wetmur, Quartin and Engelhardt, U.S. patent application Ser. No. 07/499,938, filed on Mar. 26, 1990, the latter having been disclosed in European Patent Application Serial No. 0 450 370 A1, published on Oct. 9, 1991. The contents of the foregoing U.S. patents and patent application are incorporated by their entirety into the present application.

The primers, one or more, described herein bind to specific sequences on the target nucleic acids and initiate the polymerizing reaction. While oligo deoxynucleotide primers may be preferred, polydeoxynucleotide as well as oligo and polyribonucleotide or nucleotide copolymer primers can be used (Kornberg, A. and T. A. Baker, second edition, 1992, W.H. Freeman and Co. New York, Karkas, J. D., PNAS 69:2288–2291 (1972); and Karkas, J. D. et al., Proc. Natl. Acad. Sci. U.S.A. 69:398–402 (1972)). Thus, the specific nucleic acid primers may be selected from deoxyribonucleic acid, ribonucleic acid, a DNA.RNA copolymer, or a polymer capable of hybridizing or forming a base-specific pairing complex and initiating nucleic acid polymerization. Under conditions where the primer is an oligoribonucleotide or copolymer, the primer can be removed from its cognate binding site using specific enzymatic digestion (e.g., RNase H, restriction enzymes and other suitable nucleases) such that another primer can bind and initiate synthesis. This can be used as a system for the multiple initiation of the synthesis of polynucleotide or oligonucleotide product.

Modifications, including chemical modifications, in the composition of the primers would provide for several novel variations of the invention. See, for example, U.S. Pat. Nos. 4,711,955; 5,241,060; 4,707,440; and U.S. patent application Ser. No. 07/499,938, supra. For example, substitution of the 3' hydroxyl group of the primer by an isoteric configuration of heteroatoms, e.g., a primary amine or a thiol group, would produce chemically cleavable linkers. In the case of thiol excess of another thiol in the reaction mixture will cleave the phosphorothioate linkers which is formed after the initiation of polymerization, thus allowing the DNA polymerase to reinitiate polymerization with the same primer. Thus, in this variation repeated syntheses can begin from a modified, hybridized primer providing a significant increase in the synthesis of DNA.

In another aspect of the invention, the specific nucleic acid primers are not substantially complementary to one another, having for example, no more than five complementary base-pairs in the sequences therein.

In another variation, the primer could contain some non-complementary sequences to the target, whereupon hybridization would form at least one loop or bubble which could be used as a substrate for a specific endonuclease such that the primer could be removed from the target by enzymatic digestion thus allowing reinitiation. Furthermore, the primer could contain additional sequences noncomplementary to the target nucleic acid. Thus, the specific nucleic acid primers may comprise at least one non-complementary nucleotide or nucleotide analog base, or at least one sequence thereof. The range of non-complementarity may range in some cases from about 1 to about 200 noncomplementary nucleotide or nucleotide analogs, and in other cases, from about 5 to about 20 nucleotides. Such noncomplementary base sequence or sequences can be linked by other than a phosphodiester bond.

As used herein, the term "nucleic acid producing catalyst" is intended to cover any agent, biological, physical or chemical in nature, that is capable of adding nucleotides (e.g., nucleoside triphosphates, nucleoside triphosphate analogs, etc.) to the hydroxyl group on the terminal and of a specific primer (DNA or RNA) using a pre-existing strand as a template. A number of biological enzymes are known in the art which are useful as polymerizing agents. These include, but are not limited to E. coli DNA polymerase I, Klenow polymerase (a large proteolytic fragment of E. coli DNA polymerase I), bacteriophage T7 RNA polymerase, and polymerases derived from thermophilic bacteria, such as *Thermus aquaticus*. The latter polymerase are known for their high temperature insensitivity, and include, for example, the Taq DNA polymerase I. A thermostable Taq DNA polymerase is disclosed in Gelfand at al., U.S. Pat. No. 4,889,818. Preferred as a polymerizing agent in the present invention is the Taq DNA Polymerase I. Many if not all of the foregoing examples of polymerizing agents are available commercially from a number of sources, e.g., Boehringer-Mannheim (Indianapolis, Ind.). Particularly suitable as nucleic acid producing catalysis are DNA polymerase and reverse transcriptase, or both. As used herein, "the effective amount" of the nucleic acid producing catalyst is an art-recognized term reflecting that amount of the catalyst which will allow for polymerization to occur in accordance with the present invention.

Since the rate and extent of hybridization of the primers is dependent upon the standard conditions of hybridization (Wetmur, J. G. and Davidson, N. J., Mol. Biol. 31:349 (1968)), the concentration and nucleotide sequence complexity of the total primers added to the reaction mixture will directly affect the rate at which they hybridize and accordingly the extent to which they will initiate nucleic acid synthesis. In addition, if the reaction is run under conditions where the guanosine triphosphate is replaced by inosine triphosphate or other modified nucleoside triphosphates such that the presence of this modified nucleotide in the product nucleic acid would lower the melting temperature of the product:template double helix, then at any given temperature of the reaction the extent of breathing of the double helix will be increased and the extent of binding of the primers to the target strand will be enhanced.

Furthermore, primers could displace the strands at the ends of the double stranded target and hybridize with one of the two strands and, this displacement hybridization reaction (or D loop formation reaction) is favored by adding more than one primer molecule. In general, as the total amount of the sequence complexity of the primers complementary to the target nucleic acid is increased a greater nucleic acid production is obtained (see Example 3 below).

Modification of the primers could either increase or decrease the binding of primer to the target at a given pH, temperature and ionic strength, in other words, at isostatic conditions of pH, temperature and ionic strength, e.g., ionic salt. Other primer modifications can be employed which would facilitate polymerization from the primer sites, even when the initiation site is within a double helix. For example, once an oligo primer is introduced into a target double stranded nucleic acid molecule, it such an oligo primer is modified with ethidium or any moiety that increases the meting temperature of the double stranded structure formed by the oligo and a target nucleic acid, it forms a relatively more stable single stranded structure because of the nucleotide modifications. This produces a primer initiation site. In fact, the nucleic acid precursors or the specific primers (or both) can be modified by at least one intercalating agent, such as ethidium, in which case it may be useful to carry out an additional step (d) of detecting any product produced in step (c), as set forth above. In such a step where desirable, detection can be carried out by means of incorporating into the product a labeled primer, a labeled precursor, or a combination thereof.

Another additional aspect of the in vitro process, above-described, is the inclusion of a further step of regenerating one or more specific nucleic acid primers, as described elsewhere in this disclosure, including immediately below.

As described in the summary of this invention, an in vitro process for multiple nucleic acid production is provided in which the products are substantially free of any primer-coded sequences. In such process, the removing step (d) is carried out by digestion with an enzyme, e.g., ribonuclease H. In one aspect of this invention, the nucleic acid precursors are modified or unmodified in the instance where one or more specific polynucleotide primers are used, the primers comprising at least one ribonucleic acid segment and wherein each primer is substantially complementary to a distinct sequence of the specific nucleic acid. Thus, the specific polynucleotide primers may further comprise deoxyribonucleic acid. In another feature of this particular in vitro process, the specific polynucleotide primers contain a 3'-hydroxyl group or an isoteric configuration of heteroatoms, e.g., nitrogen, sulfur, or both. In addition, the polynucleotide primers in this instance may further comprise from about 1 to about 200 noncomplementary nucleotide or nucleotide analogs.

In yet a further in vitro process for producing more than one copy of a specific nucleic acid is provided (as described in the summary), the products being substantially free of any primer-coded sequences. In this instance, unmodified nucleic acid precursors are reacted in a mixture with one or more chemically-modified primers each of which is substantially complementary to a distinct sequence of the specific nucleic acid. An effective amount of a nucleic acid producing catalyst is also provided in the mixture. As in the case of the last-described in vitro process, the removing step (d) may be carried out by digestion with an enzyme, e.g., ribonuclease H. The specific chemically modified primers are selected, for example, from ribonucleic acid, deoxyribonucleic acid, a DNA.RNA copolymer, and a polymer capable of hybridizing or forming a base-specific pairing complex and initiating nucleic acid polymerization, or a combination of any of the foregoing. The specific chemically modified primers may contain a 3'-hydroxyl group or an isosteric configuration of heteroatoms, N, S, or both, as described above in other in vitro processes. Further, the specific chemically modified primers can be selected from nucleoside triphosphates and nucleoside triphosphate analogs, or a combination thereof, wherein at least one of said nucleoside triphosphates or analogs is modified on the sugar, phosphate or base. Also as in other in vitro processes, the specific chemically modified primers may further comprise from about 1 to about 200 noncomplementary nucleotide or nucleotide analogs.

In still yet another of the in vitro processes for multiple nucleic acid production, described previously in the summary of this invention, unmodified nucleic acid precursors are provided in the mixture and reacting step (c), together with one or more specific unmodified primers comprising at least one segment, each of which primer comprises at least one non-complementary sequence to a distinct sequence of the specific nucleic acid, such that upon hybridization to the specific nucleic acid at least one loop structure is formed. As in the other instances, digestion with an enzyme, e.g., ribonuclease H, may be employed in the removing step (d). In one feature of this process, specific unmodified primers are selected from ribonucleic acid, deoxyribonucleic acid, a DNA.RNA copolymer, and a polymer capable of hybridizing or forming a base-specific pairing complex and initiating nucleic acid polymerization, or a combination of any of the foregoing. Further, the specific unmodified primers may further comprise from about 1 to about 200 noncomplementary nucleotide or nucleotide analogs, in accordance with the present invention.

The rate of hybridization of the primer to target nucleic acids and, in particular, to target double stranded nucleic acids can be facilitated by binding of the primer with various proteins, e.g., rec A proteins. For example, if the primer is modified with an intercalating agent, e.g., ethidium (or any moiety that increases the melting temperature of the double stranded structure), the addition of this primer to or with a protein such as rec A, either free or bound, would facilitate the introduction of the primer into the double stranded target. (Kornberg and Baker, supra, pages 797–800). This could produce a suitable primer initiation site.

The arrangement of primer binding sites on the template nucleic acid can be varied as desired. For example, the distance between successive primer binding sites on one strand can also be varied as desired. Also specific primers can be employed that initiate synthesis upstream of the sequence sought to be copied. Under this scenario, multiple copies of nucleic acid are made without successive denaturation or use of other enzymes or the introduction of intermediate structures for their production.

When primer sites on double stranded DNA are arranged as shown, specific DNA production is increased.

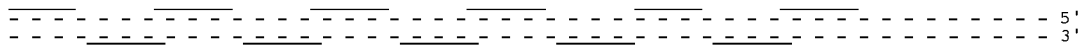
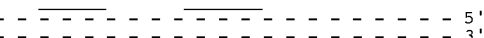

When the target sequences are substantially covered by their complementary primers, a further increase in the production of multiple copies of nucleic acid is favored due to the increase in initiation points and destabilization of the double stranded template molecule.

Finally, if an oligo is modified such that it will form a stable hybrid, even in the presence of the complementary nucleic acid strand, then the modified oligo can act as a 'helper' oligo. 'Helper' oligo in this context is defined as a oligo that does not necessarily act as a primer but will accelerate the binding and priming activity of other oligos in the vicinity to the binding site of the 'helper' oligo. Vicinity is here being defined as the location of a nucleotide sequence or the complementary nucleotide sequence close enough to the binding site of the 'helper' oligo to have the rate or extent of hybridization of the primer affected by the binding of the 'helper' oligo. The 'helper' oligo can be modified such that it does not initiate polymerization as for example through the use of a dideoxy 3' terminal nucleotide or other nucleotide with blocked 3' ends. The 'helper' oligo can also be modified in such a manner that the double helix formed by the 'helper' oligo and the target nucleic acid strand or the 'helper' and the complementary strand to the target strand is more stable or has a higher melting temperature than the equivalent double helix of unmodified 'helper' oligo and the target or the strand complementary to the target strand. Such modifications can include halogenation of certain bases, ethenyl pyrimidines (C:C triple bonds, propyne amine derivatives; the addition of ethidium or other intercalating molecules (see Stavrianopoulos and Rabbani, U.S. patent application Ser. No. 07/956,566, filed on Oct. 5, 1992, the contents of which are incorporated herein by reference and which were disclosed in European Patent Application Publication No. 0 231 495 A2, published on Aug. 12, 1987); the supplementation of the oligo with certain proteins that stabilize the double helix and any other treatment or procedure or the addition of any other adduct that serves to stabilize the portion of the double helix with the 'helper' bound or to increase the melting temperature of portion of the double helix with the 'helper' bound.

In vivo Synthesis of Nucleic Acid

This invention describes a casette or nucleic acid construct into which any nucleic acid sequence can be inserted and which can be used as a template for the production of more than one copy of the specific sequence. This cassette is a nucleic acid construct containing a sequence of interest, which within or present within, the cell produces nucleic acid product which is independent or only partially dependent on the host system. The cassette or nucleic acid construct may be characterized as a promoter-independent non-naturally occurring, and in one embodiment comprises double-stranded and single-stranded nucleic acid regions. This construct contains a region in which a portion of the opposite strands are not substantially complementary, e.g., a bubble (even comprising at least one polyT sequence), or loop, or the construct comprises at least one single-stranded region. The construct is composed of naturally occurring nucleotides or chemically modified nucleotides or a synthetic polymer in part or a combination thereof. These structures are designed to provide binding of polymerizing enzymes or primers and the modifications provide for nuclease resistance or facilitate uptake by the target cell.

Referring to the constructs (A–F) depicted in FIG. 1; the single stranded regions described in the constructs will contain coding sequences for nucleic acid primers present in the cell to facilitate initiation points of DNA polymerase in said cell. In the case of RNA polymerase, these constructs constitute promotor independent binding and initiation of RNA polymerase reaction. These constructs can be used in vitro and in vivo for production of nucleic acids. The position of the single stranded region adjacent to the double stranded specific sequence would provide a specific and consistent transcription of these specific sequences, both in vitro and in vivo independent of promotor. The replication (DNA) or transcription (RNA) products of these constructs can be single stranded nucleic acid which could have a sense or antisense function or could be double stranded nucleic acid.

Figure 1B:
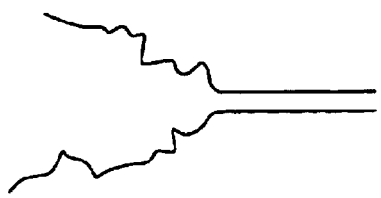
Figure 1C:
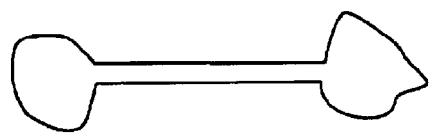
Figure 1D:
Figure 1E:
Figure 1F:
Figure 2A:
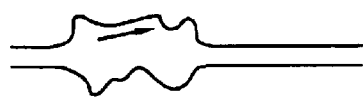
FIG. 2(A–F) depicts the functional forms of the nucleic acid constructs illustrated in FIG. 1(A–F).
Figure 2B:
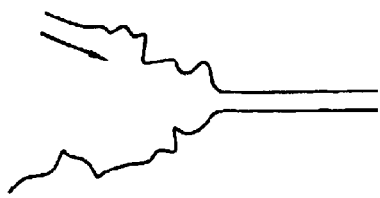
Figure 2C:
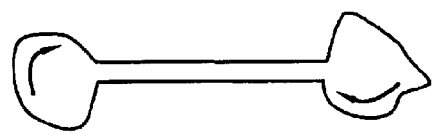
Figure 2D:
Figure 2E:
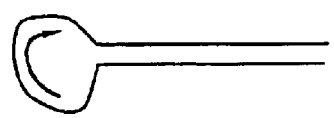
Figure 2F:

In FIG. 1A, a large bubble is located in the construct. In FIG. 1B, the two strands are noncomplementary at their ends, and thus do not form a bubble. In FIG. 1C, a double bubble is formed due to noncomplementarity at both ends. In FIG. 1D, a single-stranded region is shown in the middle of the construct leading to a partially single-stranded region (and no bubble formation). FIG. 1E depicts a bubble at one end of the construct (compare with the two bubbles in the construct shown in FIG. 1C. In FIG. 1F, a single bubble in the middle of the construct is shown. It should be readily appreciated by those skilled in this art that the above-depicted embodiments are representative embodiments not intended to be limiting, particularly in light of the present disclosure.

In vivo these constructs, with a specific primer present in the cell can initiate nucleic acid synthesis. When these primers are RNA, after initiation of nucleic acid synthesis, they can be removed by the action of ribonuclease H, thus vacating the primer binding sequence and allowing other primer molecules to bind and reinitiate synthesis. The cellular nucleic acid synthesizing enzymes can use these constructs to produce copies of a specific nucleic acid from the construct. Shown in FIG. 2(A–F) are corresponding illustrations of the constructs in FIG. 1(A–F), except that the production arrows (points and directions) are indicated.

Figure 19:
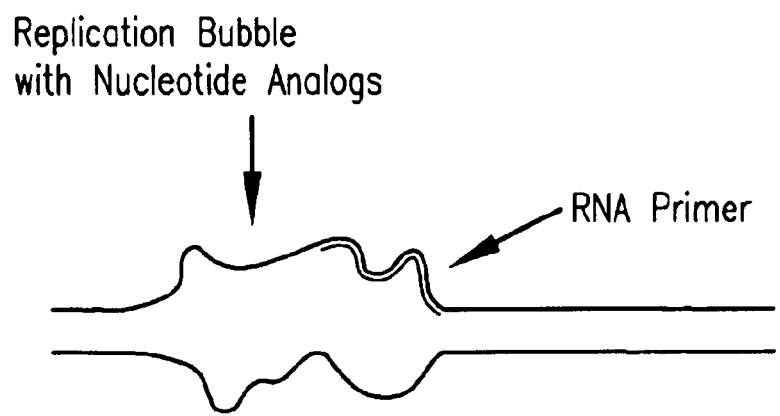
FIG. 19 illustrates a nucleic acid construct in which the host promoter serves as an independent nucleic acid production source (the progeny, FIG. 20 shows a nucleic acid construct in which single-stranded DNA product is made having a hairpin loop and which is useful for forming double-stranded product.

These constructs could contain more than one specific nucleic acid sequence which in turn could produce more than one copy of each specific nucleic acid sequence. If two independent nucleic acid products are complementary, then they could hybridize and form multiple copies of a new double stranded construct that could have the properties of the novel construct. Furthermore they could contain promoter sites such as the host promoter therefore serving as an independent nucleic acid production source (the progeny). See FIG. 19 for illustration of such nucleic acid construct in which the host promoter serves as an independent nucleic acid production source (the progeny).

The replication of this structure could result in the production of one strand of DNA product. Several alternative events may occur allowing for the formation of a second complementary strand. For example, a terminal loop could be inserted at the end of the construct such that the single-stranded product will code for the synthesis of the complementary strand using the repair enzyme. Constructs can be made that produce single-stranded DNA product that has a hairpin loop and therefore, can be used to form a double-stranded product.

Alternatively, constructs can be formed that produce nucleic acid in both polarities.

Figure 20:
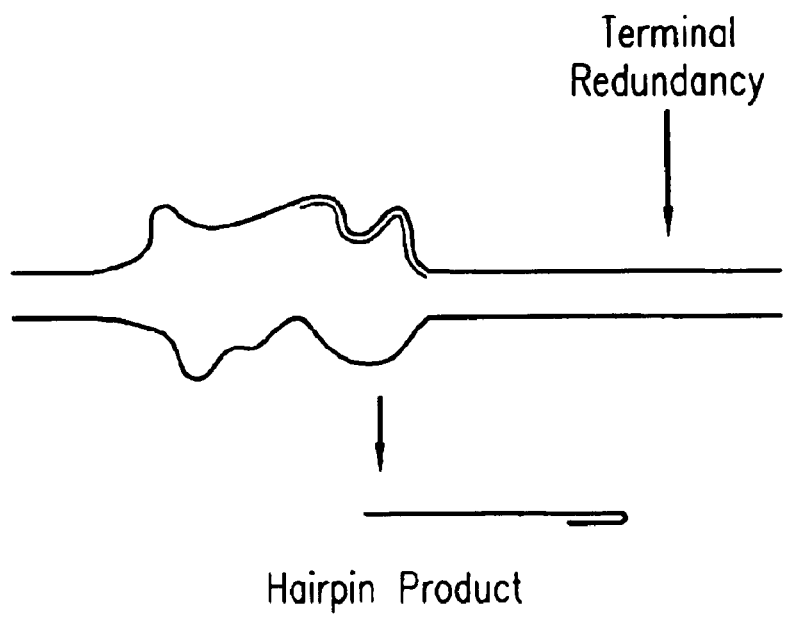

See FIG. 20 for a nucleic acid construct in which double-stranded DNA product is made having a hairpin loop and which is useful for forming double-stranded product.

An alternative approach to the production of double-stranded product is to covalently link two constructs that make complementary DNA strands.

Figure 21:
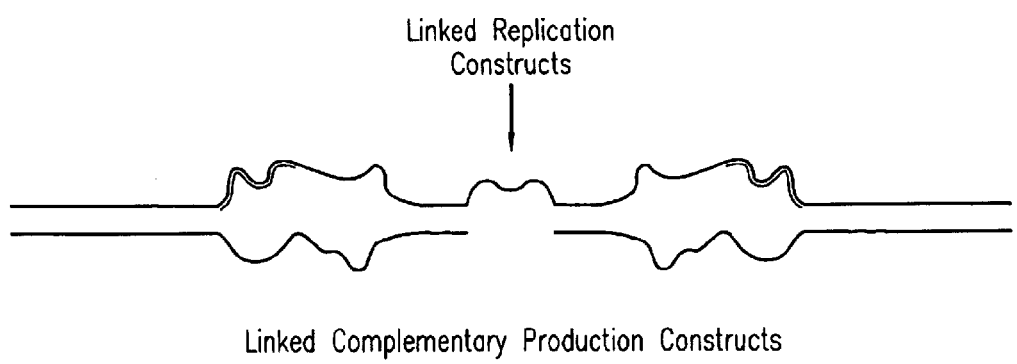
FIG. 21 depicts a nucleic acid construct for producing double-stranded product by covalently linking two constructs that make complementary DNA strands.

See FIG. 21 for a depiction of a nucleic acid construct for producing double-stranded product by covalently linking two constructs that make complementary DNA strands.

The construct can be made to contain a poly linker region into which any sequence can be cloned. The result will be a transient accumulation of expressing genes within the cell to deliver sense, antisense or protein or any other gene product into the target cell.

Figure 22:
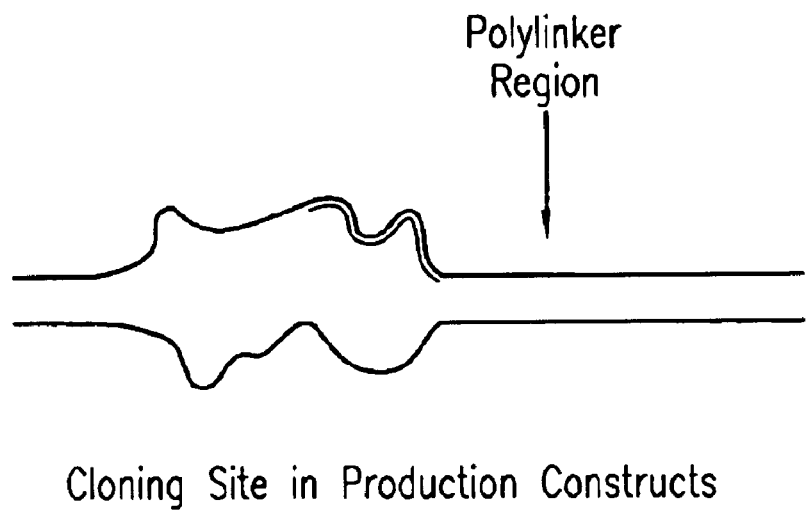
FIG. 22 illustrates a nucleic acid construct containing a polylinker region into which a desirable sequence can be cloned. The result of such a construct is a transient accumulation of gene expression within the cell to deliver sense, antisense, protein or any other gene product into the target cell.

See FIG. 22 illustrates a nucleic acid construct containing a polylinker region into which a desirable sequence can be cloned. The result of such a construct is a transient accumulation of gene expression within the cell to deliver sense, antisense, protein or any other gene product into the target cell.

Other processes within the invention herein described apply to the production of more than one copy of functional genes or antisense DNA or RNA in target cells.

Production of Primers

Primers can be produced by several methods. Single-stranded oligonucleotides in the range from between from about 5 to about 100 bases long, and preferably between from about 10 to about 40, and more preferably, between from about 8 to about 20 nucleotides. These ranges may further vary with optimally between from about 13 to about 30 for bacterial nucleic acid, and optimally between from about 17 to about 35 for eukaryote nucleotides would appear to be appropriate for most applications although it may be desirable in some or numerous instances to vary the length of the primers. Oligonucleotide primers can be most conveniently produced by automated chemical methods. In this way modified bases can be introduced. Manual methods can be used and may in some cases be used in combination with automated methods. All of these methods and automation are known and available in the art.

In addition nucleic acid primers can be produced readily by the action of T7 RNA polymerase, T3 polymerase, SP6 polymerase or any appropriate DNA or RNA polymerase on DNA templates or RNA templates containing the primer sequences extended from the corresponding RNA polymerase promoter sites or other nucleic acid synthesis start signals.

Detection of Products

DNA produced by the invention described herein can be detected by a variety of hybridization methods using homogeneous or non-homogeneous assays. DNA produced in tissues or cells, i.e., in situ, can be detected by any of the practiced methods for in situ hybridization. These include, but are not limited to, hybridization of the produced DNA with a nucleic acid probe labeled with a suitable chemical moiety, such as biotin. Probes used for the detection of produced DNA can be labeled with a variety of chemical moieties other than biotin. These include but are not limited to fluorescein, dinitrophenol, ethidium (see, for example, the disclosures of U.S. Pat. Nos. 4,711,955; 5,241,060; and 4,707,440, supra).

The hybridized, labeled nucleic acid probe can be detected by a variety of means. These include but are not limited to reaction with complexes composed of biotin binding proteins, such as avidin or streptavidin, and color generating enzymes, such as horseradish peroxidase or alkaline phosphatase, which, in the presence of appropriate substrates and chromogens, yield colored products.

In accordance with this invention, DNA production from target sequences generally requires nucleic acid precursors, e.g., adenosine triphosphate, guanosine triphosphate, thymidine triphosphate and cytosine triphosphate, present in sufficient quantity and concentration in the reaction mixture. In other applications it may be advantageous to substitute one or more of the natural precursors with modified nucleotides. For example, when the invention described herein is being applied to the detection of specific nucleic acid sequences, immobilization of the produced DNA may be desirable. In such an instance, substitution of one or more of the natural nucleotide triphosphate precursors with a modified nucleotide, e.g., biotinylated deoxyuridine triphosphate, in place of thymidine triphosphate, would yield biotin-labeled DNA. The produced DNA could be separated by its affinity for a biotin binding protein, such as avidin, streptavidin or an anti-biotin antibody. A variety of nucleoside triphosphate precursors (U.S. Pat. Nos. 4,711,955; 5,241,060; and 4,707,440, supra) labeled with chemical moieties which include, but are not limited to, dinitrophenol and fluorescein, and which can be bound by corresponding antibodies or by other binding proteins can be used in this manner. In other aspects of the invention, the produced DNA can be isotopically labeled by the inclusion of isotopically labeled deoxynucleotide precursors in the reaction mixture.

Labeled DNA, produced by the invention described herein, can function as probe nucleic acid to be used to detect specific target nucleic acid sequences.

In certain detection formats the primers may be removed from the reaction mixture by capturing the product through direct capture (Brakel et al., U.S. patent application Ser. No. 07/998,660, filed on Dec. 23, 1992, the contents of which have been disclosed in European Patent Application 0 435 150 A2, published on Jul. 3, 1991; and the contents of which are also incorporated by reference herein), or sandwich capture. (Engelhardt and Rabbani, allowed U.S. patent application Ser. No. 07/968,706, supra), or by modifying the primers at the 3' end with biotin or imminobiotin without an arm or a very short arm such that the avidin will recognize only the unincorporated primers (single stranded form) but not the incorporated due to the double stranded form and the short length of the arm. Additionally, the primer may be labeled with ethidium or other intercalating moiety. In this condition, the ethidium or other intercalating moiety may be inactivated (Stavrianopoulos, U.S. patent application Ser. No. 07/633,730, filed on Dec. 24, 1990, published as European Patent Application Publication No. 0 492 570 A1 on Jul. 1, 1992; the contents of which are incorporated by reference) in the unhybridized oligo and not in the hybridized oligo:target.

Another aspect of this invention herein described is to provide for a conjugate of a nucleic acid polymerizing enzyme (RNA polymerase) with a nucleic acid construct said nucleic acid construct contains an initiation site such as a promotor site for the corresponding RNA polymerase which is capable of producing nucleic acid both in vivo and in vitro. The enzyme could be linked directly to the nucleic acid or through a linkage group substantially not interfering with its function or the enzyme could be linked to the nucleic acid indirectly by a nucleic acid bridge or haptene receptor where the enzyme is biotinylated and the nucleic acid construct contains an avidin or vice versa or when the nucleic acid construct contains sequences for binding proteins such as a repressor and an enzyme linked to said nucleic acid binding protein (U.S. Pat. No. 5,241,060, supra, and Pergolizzi, Stavrianopoulos, Rabbani, Engelhardt, Kline and Olsiewski, U.S. patent application Ser. No. 08/032,769, filed on Mar. 16, 1993, published as European Patent Application Publication No. 0 128 332 A1 on Dec. 19, 1984, the latter having been "allowed" by the European Patent Office, and further incorporated by reference herein).

Further in regard to the just-described conjugate of the present invention, the protein in one aspect comprises an RNA polymerase or a subunit thereof and the nucleic acid construct contains the corresponding RNA polymerase promoter. The RNA polymerase can be selected from T7, T3 and SP6, or a combination of any of the foregoing. In another embodiment, the protein in the conjugate comprises DNA polymerase or reverse transcriptase and the nucleic acid construct contains at least one sequence complementary to an RNA molecule. The construct can take the form of double-stranded, single-stranded, or even partially single-stranded. Further, the nucleic acid construct in the conjugate may comprise at least one chemically modified nucleotide or nucleotide analog. The linkages of the protein to the construct are described in the preceding paragraph. The nucleic acid produced by or from this conjugate comprises deoxyribonucleic acid, ribonucleic acid, or combinations thereof, or it may be antisense or sense, or both.

As described in the summary of the invention, the above-described conjugate may be utilized in an in vivo process for producing a specific nucleic acid. In other aspects of this in vivo process, the construct is further characterized as comprising (independently) at least one promoter, at least one complementary sequence to a primer present in the cell, or codes for the protein in the conjugate, or for a protein other than the protein in the conjugate. The other protein may comprise a nucleic acid polymerase. In the instant where the polymerase comprises an RNA polymerase, the nucleic acid construct may comprise a promoter for the RNA polymerase. Further, the polymerase can be a DNA polymerase or reverse transcriptase.

(a) Direct Attachment of a Polymerase to the Construct

Figure 3A:
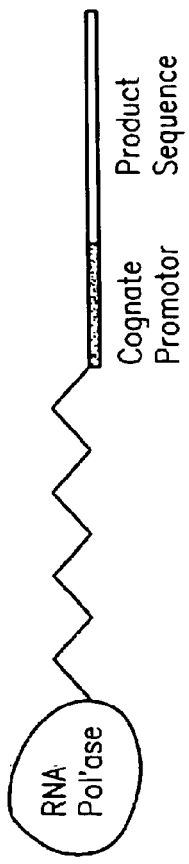
FIG. 3(A–C) is an illustration of three nucleic acid constructs with an RNA polymerase covalently attached to a transcribing cassette.
Figure 3B:
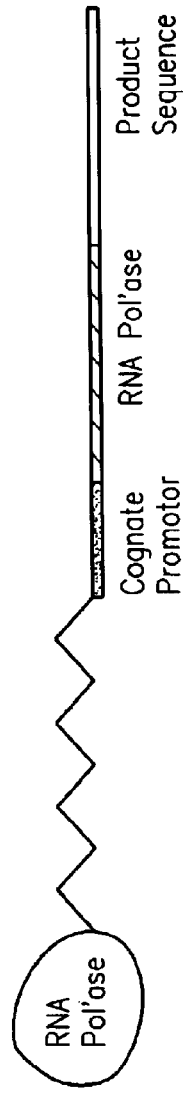
Figure 3C:
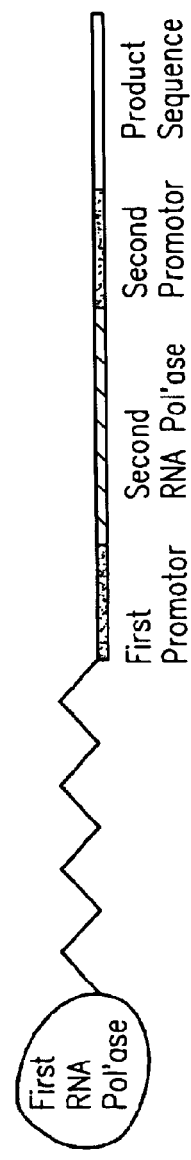

For example, if a construct containing a RNA polymerase linked directly or indirectly to a DNA construct or cassette is introduced into a cell, the RNA polymerase will transcribe the nucleic acid in the construct and is completely independent of any host RNA polymerases. Each molecule introduced into a cell will produce multiple copies of a segment of the construct. In the first iteration, the attached polymerase can produce the RNA for the target sequence itself. (See FIG. 3(A)). Alternatively, the promotor, specific for the attached polymerase, may be linked to two separate sequences, namely the polymerase gene and the target gene. See FIG. 3(B). In this instance, the amount of polymerase initiating at the promotor site will increase as the polymerase gene is transcribed and translated. Finally, the coding sequence transcribed by the $T_7$ promotor (or any specific first promotor) may produce any RNA polymerase (including $T_7$ polymerase or polymerase III or others), and this polymerase may transcribe off of another or second promotor (or off of a different strength $T_7$ or other first promotor) to produce the transcript of the target sequence. (See FIG. 3(C)).

Referring to the constructs or cassettes shown in FIG. 4(A–C), these can be derived by using standard recombinant DNA techniques. The appropriate piece of DNA can be isolated and covalently attached to the RNA polymerase under conditions whereby the RNA polymerase functions after being covalently attached to a solid matrix (Cook, P. R and Grove, F. Nuc. Acids Res, 20:3591–3598 (1992)). Methods of modifying the ends of DNA molecules for attachment of chemical moieties are well known (see, for example, U.S. patent application Ser. No. 08/032,769, supra). The transcribed product can act per se as sense or antisense RNA or it can be translated into protein. The enzyme and/or nucleic acid constructs could be modified to facilitate transport and/or achieve resistance to degrading enzymes (U.S. Pat. No. 5,241,060, supra).

(b) In vivo Amplification of Transcription

Constructs can be made that are dependent upon transcription or replication using a host polymerase. When such a construct contains a double promoter, the second promoter can be different than the first promoter or it can be a stronger or weaker version of the first promoter. Vectors can be chosen such that the constructs can either integrate into the chromosome, replicate autosomally or be replication-deficient and function only for transient expression. They can function in the nucleus or the cytoplasm it the target cell is eukaryotic. The figure below depicts various constructs or cassettes and is not limiting as to the possible variations contemplated by the present invention.

Figure 4A:
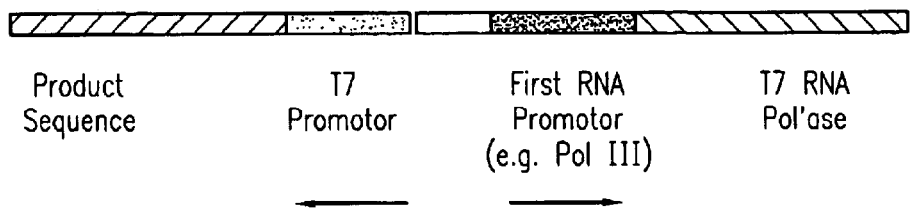
FIG. 4(A–C) illustrates three nucleic acid constructs with promoters for endogenous RNA polymerase.

Referring to FIG. 4(A), the nucleic acid construct or cassette depicted in this figure contains a promotor that codes for the production of a polymerase that is not endogenous to the target cell. For example, an SV40 or RNA polymerase III promotor that codes for a $T_7$ RNA polymerase. Transcription and translation of these transcripts by cellular machinery results in the production of active $T_7$ RNA polymerase which will utilize the $T_7$ promotor to transcribe the target sequence (Fuerst, T. R. et al., Proc Nat Acad Sci USA 83:8122 (1986)) have shown high levels of transient expression using a dual construct system with the $T_7$ RNA polymerase gene on one construct and the target gene behind the $T_7$ promotor on the other construct. The simplest iteration of this construct is that the genes coding for the polymerase code for a polymerase that exists within the cell and therefore is not recognized by the host organism as a foreign protein and does not induce an immune response.

Figure 4B:
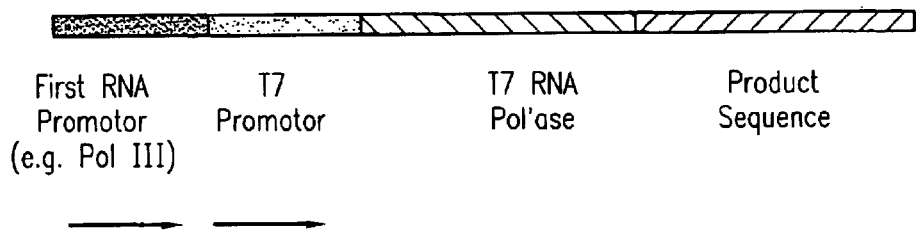

In FIG. 4(B), an additional autocatalytic cycle has been added whereby the extent of transcription of the target gene is enhanced by the production of $T_7$ RNA polymerase throughout the transient expression cycle.

Figure 4C:
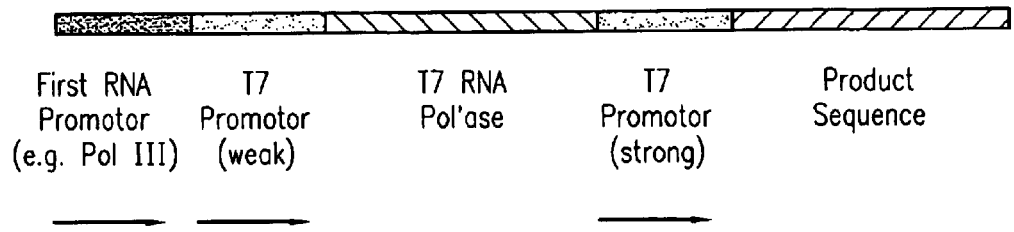

In FIG. 4(C), the construct or cassette is similar to FIG. 4(B) with the additional element that there is a down regulation of the autocatalytic cascade by competition by a high efficiency promotor with a low efficiency transcriptional promotor.

Three Constructs with Promotors for Endogenous RNA Polymerase

As described in the summary, the present invention further provides a construct comprising a host promoter located on the construct such that the host transcribes a sequence in the construct coding for a different RNA polymerase which after translation is capable of recognizing its cognate promoter and transcribing from a DNA sequence of interest in the construct with the cognate promoter oriented such that it does not promote transcription from the construct of the different RNA polymerase. In one feature of this construct, the host promoter comprises a prokaryotic promoter, e.g., RNA polymerase, or eukaryotic promoter, e.g., Pol I, Pol II, Pol III, or combinations thereof, such prokaryotic or eukaryotic promoter being located upstream from the host promoter. The second RNA polymerase may be selected from various members, including T7, T3 and SP6, or combinations thereof. The DNA sequence of interest may comprise sense or antisense, or both, or it may comprise DNA or RNA, or still yet, it may encode a protein. The construct may further comprise at least one chemically modified nucleotide.

Additionally, promotors that will be read by polymerases within the target cell can be linked to the production of additional polymerase specific for that promoter or other promoters. The polymerases can be for example, T7 polymerase, RNA polymerase III, or any other polymerase. A second promotor keyed sequence can be in the construct such that a second polynucleotide can be synthesized from the construct. It can code for the production of antisense or sense RNA or DNA molecules. These constructs or cassettes can be created using standard recombinant DNA techniques.

The property and structure of all nucleic acid constructs provided in accordance with this invention is applicable to each other in combination, in toto or in part. That is to say, in the conjugate comprising a protein and a nucleic acid construct, the construct could include, for example, chemical modification and bubble structure or single-stranded regions for primer binding sites or RNA initiation sites. Other variations would be recognized by those skilled in the art in light of the detailed description of this invention.

The examples which follow are set forth to illustrate various aspects of the present invention but are not intended to limit in any way the scope as more particularly set forth in the claims below.

DESCRIPTION OF THE PREFERRED EMBODIMENTS

EXAMPLES

Example 1

Primers

A set of twenty single stranded oligonucleotide primers, fifteen nucleotides long, were chemically synthesized.

The first set of 10 primers was complementary to one strand of M13mp18 replicative form (RF) starting at base 650 and extending to base 341. An interval of 15 nucleotides separated successive primers. The second set of 10 primers contained sequences identical to the single-stranded M13mp18 phage genome starting at base 351 and extending to base 635, again with 15 nucleotide gaps separating successive primers. There is a complementarity of 5 bases between opposing primers, but at an ionic concentration of 0.08M NaCl and 45° C. these primers will not hybridize to each other. The sequences of the primers are shown in FIG. 6.

ARRANGEMENT OF OLIGONUCLEOTIDE PRIMERS IN AMPLIFICATION REACTION

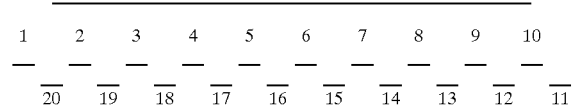

Primer 1 begins at base 650 and primer 11 begins at base 351.

Example 2

Amplification Target

Figure 7:
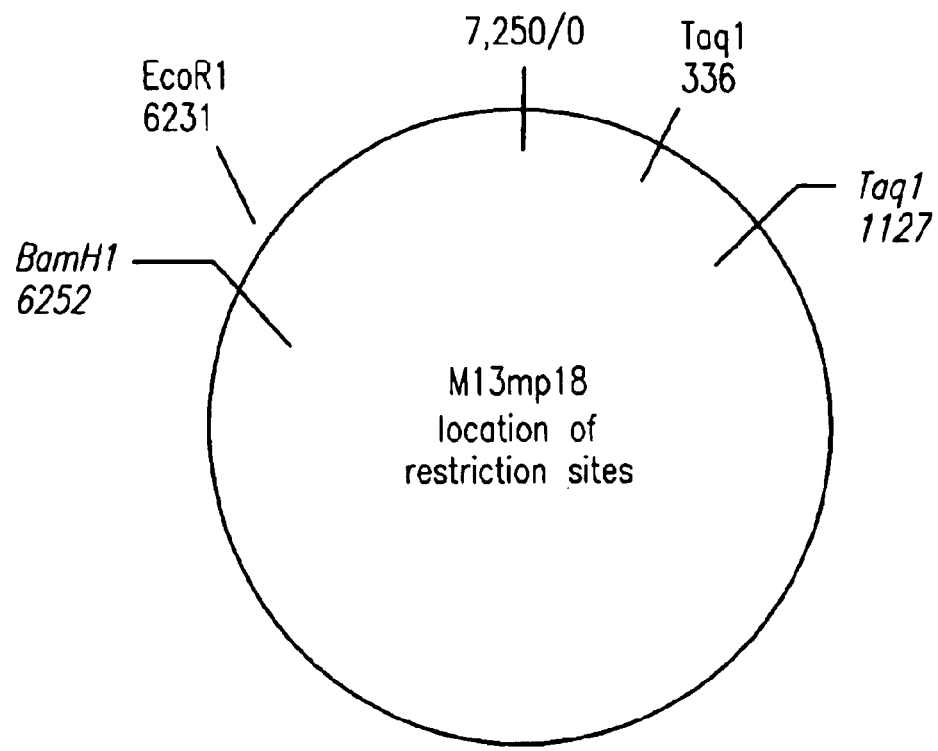
FIG. 7 illustrates appropriate restriction sites in M13mp18.

The target of amplification was the M13mp18 RF. This was digested with either Taq1 or a combination of BamH1 and EcoR1. EcoR1 and BamH1 cut at sites close to each other and digestion with either enzyme alone would transform the circular RF molecule into a linear DNA molecule. The Taq1 enzyme digests M13mp18 RF yielding 12 fragments. The sequence to be amplified (nucleotides 351 to 650) was flanked in the BamH1/EcoR1 digested RF by two regions, 1,371 bases and 5,601 bases, and Taq1-digested M13mp18 RF was flanked by regions of 15 and 477 nucleotides (see FIG. 7).

In amplification experiments, the restriction digests were used without any further purification. For amplification, a control of irrelevant DNA (calf thymus) was employed.

The precursors were added in 50 $\mu$l aliquots. One 10 $\mu$l aliquot of the precursors was mixed with 90 $\mu$l $H_2O$ and loaded on a glass fiber filter, dried and counted. The counts were multiplied by 5 and divided by 160 (nmoles in the incubation mix). Specific activity is the cpm/nmoles of nucleotides.

Amplification is measured as follows. The total counts are determined and this number is divided by the specific activity of the precursors to determine the number of nanomoles of incorporation. The target (in n grams) is divided by 330 (average molecular weight of nucleotide) to determine the nanomoles of input target phosphate. The amplification is then calculated by dividing the nanomoles of product by the nanomoles of input target.

Example 3

The Effect of Primer Concentration on the Amplification of Target DNA.

An incubation mixture of 130 $\mu$l contained the following reaction components: 40 mM sodium phosphate, pH 7.5, 400 $\mu$M each of the four deoxynucleotide triphosphates, 5 mM dithithreltol, 40 ng of Taq1-digested M13mp18 RF (containing 3.5 ng of the Taq1 fragment to be amplified), and all 20 primers (at 0.04 OD/ml, 0.4 OD/ml or 0.8 OD/ml) and 15 units of Klenow fragment of DNA polymerase. The mixture was left at room temperature for 20 minutes in order to allow the enzyme to cover all of the initiation sites on the template. The polymerization was then initiated by the addition of $Mg^{++}$, 7 mM final concentration, and the tubes were placed in a 45° C. bath. After 1 hour an additional 15 units of the enzyme were added, and the incubation was continued for another hour. The reaction was stopped with 100 $\mu$moles of EDTA, 100 $\mu$g sonicated calf thymus DNA were added, and the nucleic acids were precipitated with 1.0 ml of cold 10% TCA for 60 minutes at 0° C. The mixture was filtered through a glass fiber filter, the filter was washed 3 times with cold 5% TCA, then twice with ethanol, dried and counted in a Beckman liquid scintillation counter.

The specific activity of the nucleotide precursors was 9,687 cpm/nmole. The tagged Taq1 DNA fragment contained 0.0106 nmoles of nucleotides.

| Primer Concentration | Incorporation (cpm) | Incorporation (nmoles nucleotide) | Amplification |
|---|---|---|---|
| 0.04 OD/ml | 32,482 | 3.35 | 316 |
| 0.4 OD/ml | 366,260 | 37.8 | 3566 |
| 0.8 OD/ml | 512,260 | 52.88 | 4988 |

Example 4

The Random Priming Activity of the Primers on Calf Thymus DNA.

To test for the effect of the primers on the background, an assay was performed, as described in the preceding example (Example 3 above), in which background was determined with and without primers as well as with and without melting of the calf thymus DNA.

The amplification conditions were the same as in Example 1 except that only 5 ug (15.0 nmoles) calf thymus DNA were used as a target. The DNA employed was double stranded or heated at 100° C. for 10 minutes in the presence or absence of primers (0.4 OD/ml each) before being chilled on ice.

| Double Stranded DNA | Melted DNA | Primers | Incorporation cpm | Incorporation umoles | Amplification |
|---|---|---|---|---|---|
| + | | | 239,100 | 24.68 | 1.64 |
| + | | + | 276,540 | 28.54 | 1.90 |
| | + | + | 556,560 | 57.45 | 3.83 |
| | + | | 28,432 | 2.93 | 0.19 |

This experiment suggests that the random priming activity of the primers is not substantial, that incorporation on double stranded DNA is due to the nicks on the DNA molecules, and that melting abolishes to a large extent the priming positions on the irrelevant DNA.

Example 5

Amplificlation of the M13 Fragment in the Presence of a Large Excess (1500-Fold) of Irrelevant DNA The amplification conditions were the same as in Example 1. Primers (0.4 OD/ml), 5 ug calf thymus DNA and 40 ng M13mp18 DNA containing 3.5 ng of fragment were employed in this example.

| Calf Thymus DNA | M13mp18 DNA | Incorporation cpm | Incorporation nmoles | Amplification |
|---|---|---|---|---|
| + | | 575,440 | 59.4 | 3.96× |
| | + | 338,900 | 35.0 | 3,300× |
| + | + | 713,440 | 73.6 | |

The experimental results above show that the target can be amplified in the presence of large amounts of irrelevant DNA. The net amplification was 1,343 even though in this case the target DNA inhibits the amplification of the irrelevant DNA by competing for initiation points. It is possible that the amplification was even larger.

Figure 8:
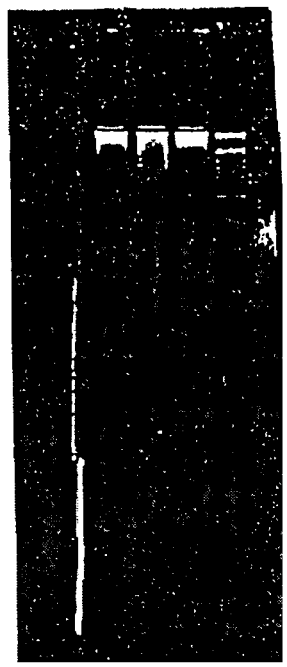
FIG. 8 is an agarose gel with a lane legend illustrating the experimental results in Example 5 in which amplification of the M13 fragment was carried out in the presence of a large excess (1500 fold) of irrelevant DNA.

These experimental results were also analyzed by running the samples on a 2% agarose gel. In FIG. 8 it can be seen that the calf thymus template (lane 3) only gives high molecular weight DNA bands composed of a mixture of input DNA as well as DNA synthesized by random priming (as seen in the incorporation figures in the Table above given for this example). On the other hand, it can be seen that the mp18 template (lane 2) gives a distinct pattern of lower molecular weight bands, and in lane 1, similar bands are observed when the mp18 template was mixed with 1500 times as much calf thymus DNA demonstrating that the foreign DNA did not significantly affect the amplificiation of DNA from the mp18 template.

Example 6

Amplification of Different Restriction Digests

The incubation conditions were the same as in Example 4. Forty nanograms of total M13mp18 DNA were used in each experiment with 0.4 OD/ml primers. In one case, the M13mp18 DNA was cut in only one position (using EcoR1) leaving the fragment to be amplified flanked by two large pieces. In the other case where the RF was treated with Taq1, the fragment was contained in one 639 base pair fragment. The specific activity of the precursors was 8.385 cpm/nmole.

| | Incorporation cpm | Incorporation nmoles |
|---|---|---|
| Large Fragment | 393,480 | 46.92 |
| Small Fragment | 262,808 | 31.34 |

These experimental results show that the enzyme does not extend polymerization very far from the region where the primers hybridize, otherwise a much larger incorporation using the large piece would have been otherwise expected because the elongation of the primers by the enzyme can extend in both directions.

Example 7

A Comparison of Synchronized and Unsynchronized Reactions

In all of the preceding experiments, the enzyme was preincubated with the target-primer mixture to allow binding of the enzyme at the 3' end of the hybridized primers on the target, followed by the addition of magnesium to initiate polymerization. The conditions were the same as in Example 1.

To assay the effect of this synchronization on the extent of the reaction, the incorporation in a synchronized reaction was compared to an unsynchronized reaction initiated by adding magnesium to the complete reaction mix before enzyme addition. The reaction conditions are described in Example 3. The specific activity was 9687 cpm/nmole.

| | Incorporation cpm | Incorporation nmoles | Amplification |
|---|---|---|---|
| Synchronized | 495,080 | 51.1 | 4818 |
| Unsynchronized | 416,380 | 42.9 | 4052 |

The results above demonstrate that synchronization of the reaction is not essential for the amplification reaction.

Example 8

The Effect of Variations of the Reaction Conditions on the Product Produced by the Procedure of Example 3

Figure 9:
FIG. 9 is an agarose gel with a lane legend illustrating the results in Example 8 in which the effect of variations of reaction conditions on the product obtained in Example 3 was investigated.

A reaction was performed according the the reaction conditions of Example 3 in which twenty primers were added to the reaction mixture as well as the Taq 1 fragments (40 nanograms, i.e., 3.5 nanograms of insert that will hybridize with the primers) described in Example 3 with the exception that the buffer was altered. In the first lane of the gel shown in FIG. 9, the reaction was performed without target DNA added. In lane 2 the reaction was performed in a phosphate buffer (0.04 M, pH 7.5). Lane 3 contains the molecular weight buffers of Msp I digestion of pBR322 DNA. In the fourth lane the reaction was performed in which the phosphate buffer was substituted by MOPS buffet at 0.1 M and pH 7.5 (measured 25° C.). It can be seen that the reaction in the phosphate buffer produced an agglomeration of DNAs that when dissociated by heat or other double helix disrupting agents lead to an number of products of a size smaller than the agglomeration structures. The size distribution of the products in the MOPS-buffered reaction corresponds to the distances between certain of the oligo primer binding sites. The smallest is approximately 76 nucleotide pairs in size which is approximately the distance between the closest specific oligo primer binding sites.

Example 9
Effect of Various Buffers on the Amplification Reaction.

The buffer used for the amplification reaction can have significant effects upon the degree of amplification. In the following example, phosphate buffer (which was employed in Example 7) was compared with the following zwitterion buffers:
4-morpholinoethyl sulfonate (MES),
4-morpholinopropionyl sulfonate (MOPS),
N-dimethylaminobutyric acid (DMAB), and
N-dimethylglycine (DMG).

Trizma base was used to adjust MES or MOPS to pH 7.5, DMAB to pH 7.8, and DMG to pH 8.6. In the previous experiments, 4.0 ng of mp18 (containing 3.5 ng of the target fragment) was used as a template. In this experiment, the amount of template was reduced ten-fold compared to those experiments (4 ng of mp18; 350 pg of target fragment). Other changes in the experimental procedure was the omission of DTT and the use of a single addition of 10 units of Klenow polymerase. $Mg^{++}$ and dNTP concentrations (7.5 mM and 400 $\mu$M each dNTP) were as described previously.

As before, reactions were preincubated at room temperature for 30 minutes prior to the addition of the $Mg^{++}$. After addition of $Mg^{++}$, reactions were immediately transferred to a 45° C. water bath and incubated for 4 hours. The reaction was stopped by the addition of 5 $\mu$l of 500 mM EDTA to give a final concentration of approximately 20 mM.

For evaluation of the extent of polymerization, an aliquot of 40 $\mu$l (out of a 120 $\mu$l incubation mix) was mixed with 50 $\mu$g of sonicated calf thymus DNA and precipitated on ice with 1 ml of 10% TCA. After one hour, the precipitate was collected on glass fiber filters, washed 3 times with 5% of cold TCA, 2 times with 95% ETOH, dried and counted in a liquid scintillation counter. The input was measured by the addition of radioactive precursor onto a filter without precipitation with TCA and counted as before. The results are given in the table below. As controls, the reactions were also carried out without the addition of any target template.

Compared to the no template control, the highest efficiency of amplification was obtained with the DMAB buffer. The results of this experiment demonstrated that an amplification of the target region approaching 37,000 fold could be obtained. It should be noted that another buffer, MES, gave higher incorporation, but the no template control demonstrated that there was non-specific polymerization leading to a net amplification of only 20,000 fold. The next best buffer system was DMG where net amplification was over 26,000 fold, followed by MOPS with 20,000 fold amplification.

The results of this experiment were also analyzed qualitatively by ethanol precipitating the remaining 80 $\mu$l of the reaction mixtures, resuspending them in 80 $\mu$l of TE buffer and running 10 $\mu$l aliquots on 2% agarose gels. These results are shown in FIG. 10 and agree with the results shown in the table above.

Example 10

Incorporation of radioactive precursors measures total synthesis of DNA including both specific as well as template-independent DNA synthesis. Oligos No. 1,3,5,7,9, 12,14,16,18 and 20 from Example 1 were employed in a series of amplification reactions. This limited number was chosen such that there would be a region within the amplicon that does not correspond to any of the primers, allowing the use of a 30 base probe (bases 469 to 498) labeled with biotin that corresponds to this open region.

The experimental design was to use DMAB and DMG buffers. Example 9 had previously shown little or no template-independent synthesis with DMAB and substantial template-independent synthesis with DMG. Reactions with and without Taq digested mp18 were carried out. The reaction mixtures were precipitated with ethanol, resuspended in TE buffer and aliquots were electrophoresed through a 2% agarose gel. A southern blot was made from this gel and probed with 200 ng/ml labeled oligo in 31% formamide/2×SSC at 25° C. for 2 hours and washed 3× with 0.1×SSC/0.1% Triton X-100 for 5 minutes each at 37° C. Membranes were developed using an alkaline phosphate detection system obtained from Enzo Biochem, Inc.

Figure 11:
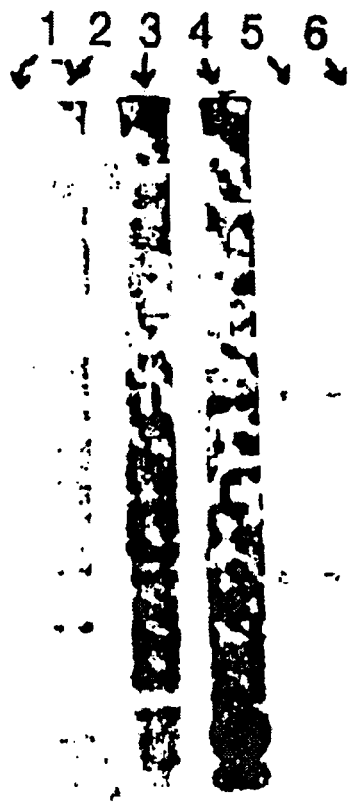
FIG. 11 is a southern blot (with lane legend) obtained from Example 10 in which two buffers, DMAB and DMG, were separately employed in nucleic acid production.

As seen in FIG. 11, this set of experiments demonstrates that the product of the amplification is strongly dependent upon the specific buffer used in the reaction. The best results were obtained with DMAB buffer where essentially no incorporation (data not shown) or hybridization (FIG. 11, lane 1) with the reaction mixture from the no template control sample. The template dependent synthesis with DMAB (FIG. 11, lane 2) produced DNA that hybridized with the labeled probe.

The nature and origin of the non-template derived synthesis achieved with DMG buffer (FIG. 11, lane 3) is still under current study.

| Buffer | Incorporation From Template (in cpm) | No Template Control (in cpm) | Template-Specific Incorporation (in cpm) | Net Synthesis (nanomoles) | Amplification Factor |
|---|---|---|---|---|---|
| Phosphate | 4,008 | 2,628 | 1,380 | 0.255 | 240 |
| MES | 299,367 | 212,778 | 86,589 | 16.03 | 15,123 |
| MOPS | 184,500 | 49,521 | 114,979 | 21.28 | 20,075 |
| DMAB | 207,239 | 5,859 | 211,380 | 39.13 | 36,915 |
| DMG | 182,655 | 32,012 | 150,643 | 27.89 | 26,311 |

Example 11
Determination of the Nature of the Ends of the Amplified Product

If the product strands act as the template for polymerization of nucleic acid then the products should have blunt ends. One method of assaying for the presence of blunt ends is based on the notion that these molecules will undergo blunt end ligation. Molecules with 'ragged' ends (single stranded tails on the 3' or 5' end) will not participate in the ligation reaction.

Because the amplified product is initiated using chemically synthesized primer molecules, the 5' ends will not under phosphorylation. The first step of this proof will be to phosphorylate the 5' ends of both single stranded and double stranded molecules. These 5' phosphorylated molecules will then be ligated using the T4 DNA ligase. The unamplified DNA will act as the negative control and a PCR-generated amplicon will act as the positive control.

Figure 12:
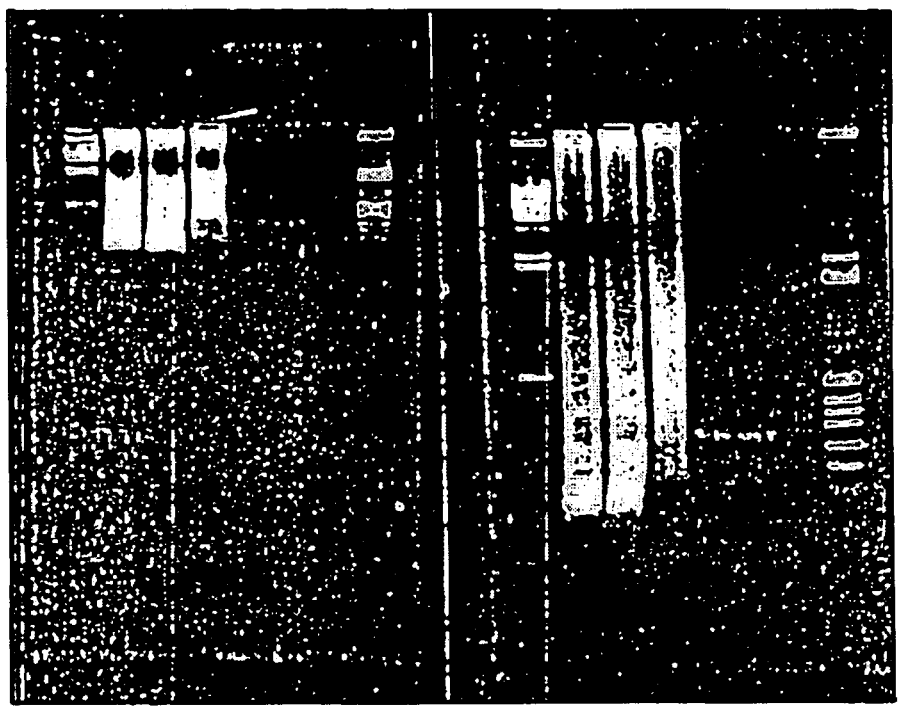
FIG. 12 is an agarose gel and lane legend obtained in Example 11 in which the nature of the ends of amplified product was investigated.

As can be seen in the gel reported in FIG. 12, T4 ligase treatment increases the molecular weight of the amplified product selectively. This is most apparant in lane 4 of FIG. 12, where there is an appreciable increase in size observed as a result of the completed ligation reaction.

The positive control with the PCR-generated amplicon (primed by oligos initiating at nucleotide 381 and from nucleotide 645 of the template which predicts an amplicon of 264 nucleotides) also show a shift in position after ligation (lane 7). Because there was not much DNA included in this reaction, the appearance of a spectrum of multimers of the amplicon was not observed, but the loss of material from the position of the unligated material (lanes 5 and 6) was noted. Some material left at the position of the untreated amplicon in lane 7 was also noted. It is possible that this material does not participate in the ligation reaction because of the addition of A to the 3' end of the amplicon which is a property of the Taq polymerase.

Example 12
Amplification from Non-denatured Template

Figure 13:
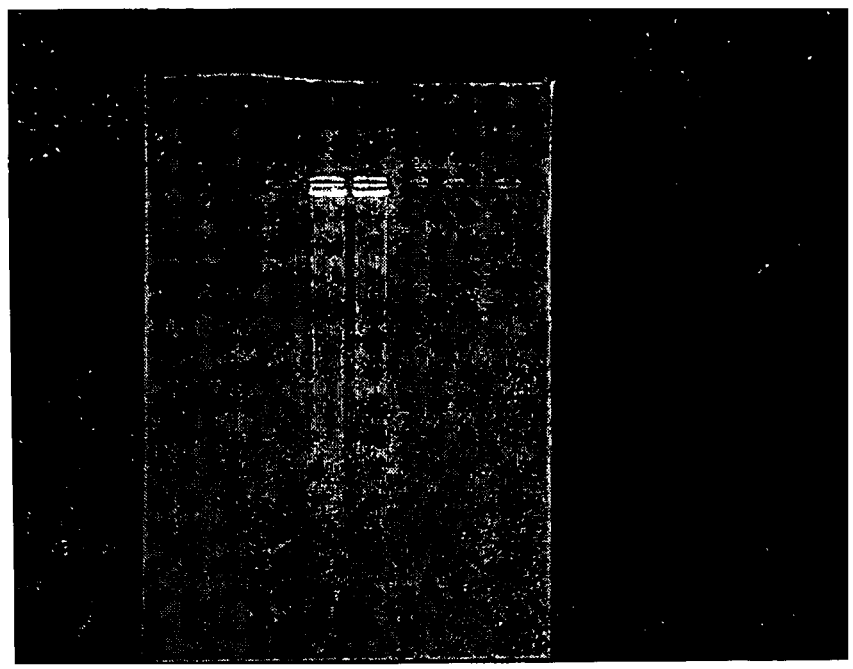
FIG. 13 is an agarose gel obtained in Example 12 in which amplification from non-denatured template was examined.

To explain the high level of amplification in this system, it was assumed that some of the primers might be able to initiate DNA synthesis by inverting the ends of double-stranded DNA products synthesized during amplification. This "breathing" was demonstrated in the following experiment. The template was a blunt-ended double-stranded DNA molecule obtained from Dr. Christine L. Brakel, the blunt ends extending from bases 371 to 645 in the mp18 DNA sequence. These ends exactly match primers Nos. 1 and 12 (described in Example 1). In this experiment, no radioactive precursors were used. Analysis was performed by gel electrophoresis through 2% agarose. Reagent conditions were the same as Example 10 where DMG was used as the buffer, but only 2 primers, No. 1 and No. 2 were used and no denaturation of the starting template was performed. In FIG. 13, for comparison purposes, the same amount of DNA was used as the input on the gel (lane 1). In lane 2, no template was added. In lane 3, the complete reaction mix is shown. In lane 4, 12 times as much DNA as the template input in either lanes 1 or 3 has been included as a size marker. In both lanes 2 and 3, some non-specific synthesis can be seen, but the specific copying of the template can clearly be distinguished in lane 3. Therefore, as lane 3 indicates, newly synthesized DNA of the same size as the input was formed using non-denatured double-stranded DNA, proving that the double-stranded blunt ends can serve as initiation points for replication.

Example 13
Amplication from RNA Template

Figure 14:
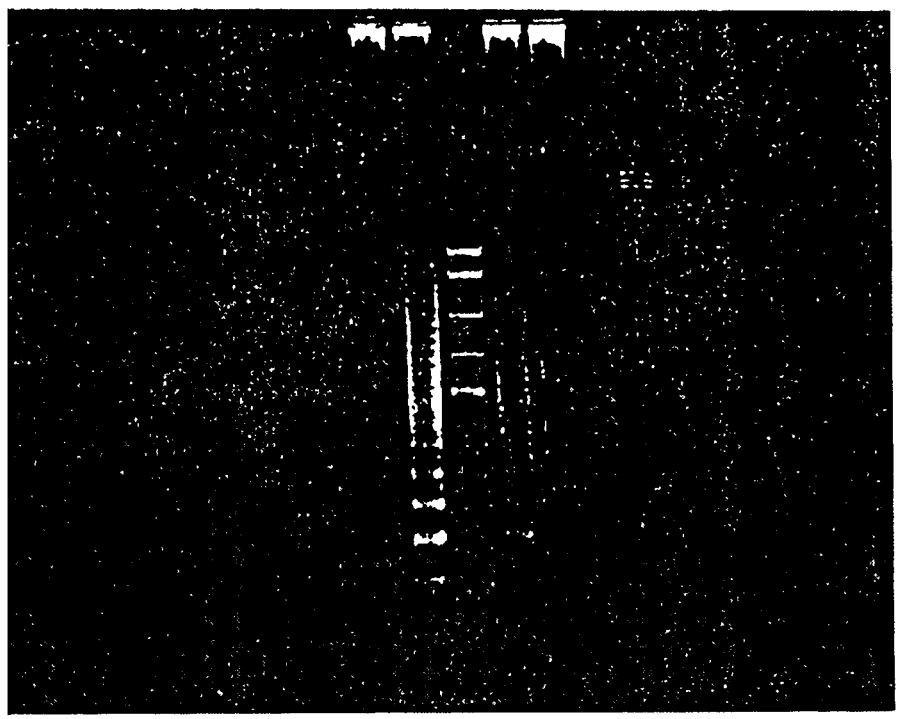
FIG. 14 is an agarose gel obtained in Example 13 in which amplification from an RNA template was examined.

Although it has been demonstrated by the present invention that DNA can be amplified, it would be useful, however, to also be able to employ RNA as a potential template. Accordingly, the double-stranded DNA molecule used in Example 12 was ligated into the Sma I site of a vector pIBI31 (obtained from International Biotechnology Corp) that contains a promotor for T7 RNA polymerase. Using standard methodologies, an RNA transcript was synthesized encompassing the same sequences used in example 12. This transcript was amplified using standard conditions with all 20 primers in DMG buffer. Taq digested mp18 DNA was used as a control. As seen in FIG. 14 there was extensive synthesis. There are characteristic bands that appear in lane 4, the reaction with the RNA template, as well as in lane 2, the reaction with the DNA template that do not appear in the template independent synthesis seen in lanes 1 and 5.

Figure 15:
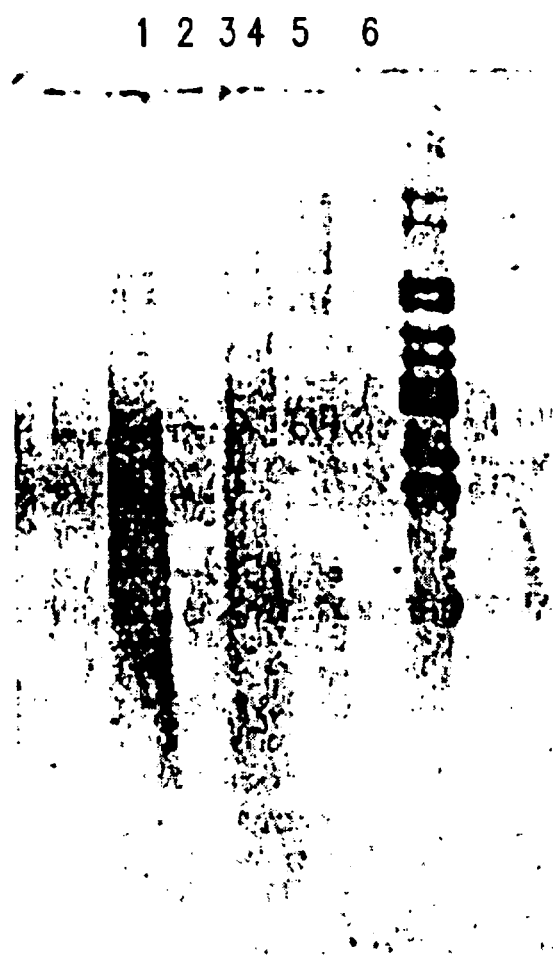
FIG. 15 is a southern blot of the gel obtained in FIG. 14.

This demonstrates that the system is capable of utilizing the RNA transcript as a template without the introduction of any other enzyme besides the Klenow, thus proving that the Klenow enzyme can be used as a reverse transcriptase as indicated in the disclosure. This result was studied further by making a Southern blot of the gel seen in FIG. 14 and probing with nick-translated biotinylated mp18 DNA using a nick translation kit obtained from Enzo Biochem. Inc. As seen in FIG. 15, there was little or no hybridization of the probe to the reaction product of the template independent reactions (lanes 1 and 5) whereas extensive hybridization was observed with the RNA derived reaction (lane 4) as well as the DNA template derived reaction (lane 2), as expected.

Example 14
Strand Displacement Using Ethidium-Labeled Oligonucleotides

Figure 16:
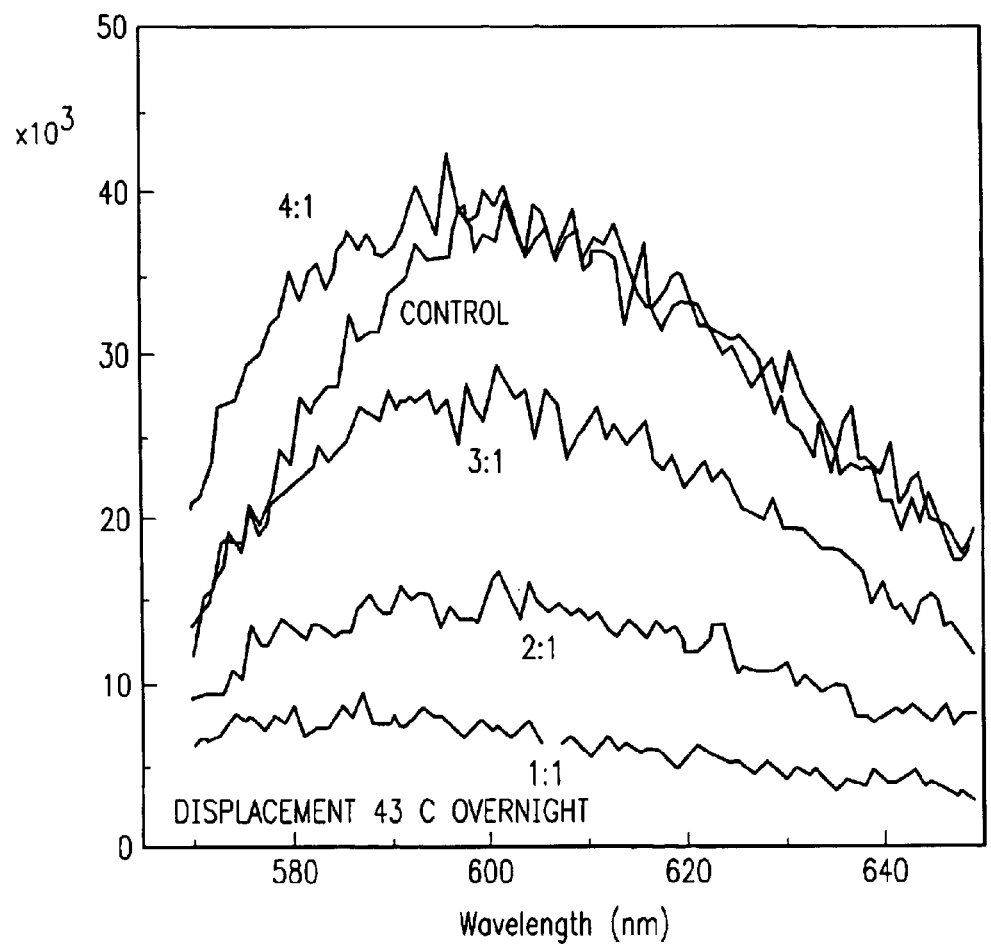
FIG. 16 is a fluorescence spectrum illustrating the results obtained in Example 14 in which the phenomenon of "strand displacement" using ethidium-labeled oligonucleotides in accordance with the present invention was investigated.

Three oligonucleotides with the sequence listed in FIG. 16 were prepared and labeled F1, F1C and F3. The unlabeled complement of F1C was hybridized to unlabeled F1. The ratio of F1C:F1 for the hybridization was 1:2. (F1C at a concentration of 0.13 O.D/ml and F1 at a concentration of 0.26 O.D./ml.) Hybridization was performed in 1×SSC for two hours at 45° C.

Aliquots of the hybrid were mixed with different amounts of ethidium-labeled F1 (F1E) in 1×SSC and incubated for 18 hours either at 43° C. or at 37° C. The ratios of F1E oligo to the unlabeled oligo F1C was 1:1, 2:1, 3:1 and 4:1. (The 1:1 reaction contained 0.0325 O.D of the F1E, 0.065 O.D. of F1 and 0.0325 O.D. of F1C.) At the end of the incubation period, 50 μl of each mixture was incubated with 50 μl of diazonium mixture for 5 minutes at room temperature. To prepare the diazonium mixture, 10 μl of the diazonium stock solution, (50 mM in 1M HCl), was added to 100 μl of cold dilution buffer, (1×SSC and 0.2 M KHCO$_3$, prepared fresh). The diazonium stock solution is stored at −20° C.

Figure 17:
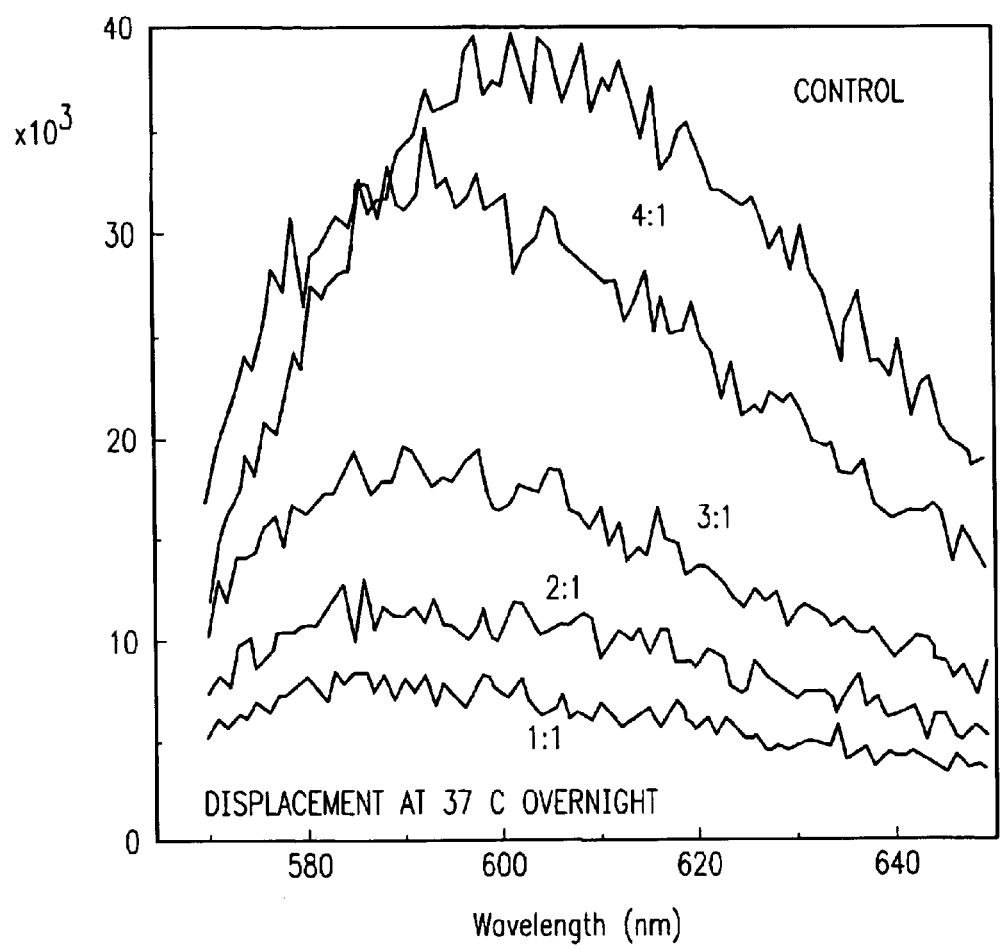
FIG. 17 is a fluorescence spectrum illustrating the results obtained in Example 15 in which a T7 promoter oligonucleotide 50 mer labeled with ethidium was employed to study its effect on in vitro transcription by T7 and T3 polymerases from an IBI 31 plasmid (pIBI 31-BH5-2) and from a BlueScript II plasmid construct (pBSII//HCV).

Under these conditions the diazonium will destroy the fluorescence associated with the ethidium in single stranded oligonucleotides. See, e.g., European Patent Application Publication No. 0 492 570 A1, published on Jul. 1, 1992, based on priority document, U.S. patent application Ser. No. 07/633,730, filed on Dec. 24, 1990, the contents of which are incorporated by reference. But the diazonium will not destroy the fluorescence associated with the ethidium that has intercalated into the double stranded DNA. The survival of the ethidium, under these reaction conditions, is a measure of the extent of formation of a double helix by the ethidium-labeled oligonucleotides, thus indicating displacement of the non-ethidium containing strand by that of the ethidium labeled. This property of the ethidium labeled oligonucleotides by primers can be usefully employed to facilitate initiation of polymerization on double stranded templates. As seen in the figure in FIG. 17, the ethidium-labeled oligo displaces the non-ethidium-labeled oligo better at 43° C. than at 37° C.

Example 15
T7 Promoter Oligonucleotide 50 Mer Labeled with Ethidium

An oligonucleotide 50-mer including the T7 promoter region of IBI 31 plasmid constructs (plasmid sequences derived from manufacturer, International Biotechnology, Inc.) was synthesized. Its sequence is as follows:

3'-TAC T*AA T*GC GGT* CT*A T*AG T*T--AA TCA TGA AT--T AAT* TAT* GCT* GAG T*GA T*AT* C-5', where T* represents allylamine dU, and therefore ethidium modification and the 10 base sequence set off by dashes (--AA TCA TGA AT--) was introduced to provide a restriction enzyme site.

Example 16
Use of the Oligonucleotide 50-Mer to Regulate RNA Synthesis In Vitro

This nucleotide is complementary to the ATG strand of the lac z gene of IBI 31, and also contains a 10-base sequence for use in restriction enzyme digestion. The oligonucleotide 50-mer also contains sequences overlapping the T7 promotor in the IBI 31 plasmid constructs. Thus, it might be expected to interfere with in vitro transcription by T7 RNA polymerase even though the sequences in this oligo are entirely upstream of the start of transcription by T7 RNA polymerase. Because the plasmid constructs contain opposing T7 and T3 promotors, this also means that the oligo 50-mer is identical in sequence to the RNA that is made by the T3 RNA polymerase in vitro.

The effect of this oligonucleotide on in vitro transcription by T7 and T3 polymerases from an IBI 31 plasmid construct (pIBI 31-BH5-2) and from a BlueScript II plasmid construct (pBSII/HCV) was studied. See FIG. 18 which contains the same target sequences, but in a "split" arrangement. The polylinker sequences of these plasmids are given in FIG. 18. Comparing the effect of the oligo on these two different target template serves to partially control for the possible non-specific inhibitory effects of ethidium groups on the RNA polymerases because the oligonucleotide would be expected to inhibit transcription from any template containing an appropriate promotor regardless of the "split" if the effect were due to the oligo's interaction with the polymerase rather than with the template.

At a concentration of 60-fold excess of oligonucleotide (0.6 μM final) over plasmid with either the allylamine labelled oligonucleotide of the ethidium labelled oligonucleotide in a transcription reaction mixture, the following results were obtained:

| Plasmid Transcribed | Polymerase Used | Oligo Used | nanomoles Incorporated | % of control |
|---|---|---|---|---|
| pIBI 31-BH5-2 | T3 | None | 236 | 100 |
| pIBI 31-BH5-2 | T3 | Allylamine labeled | 233 | 99 |
| pIBI 31-BH5-2 | T3 | Ethidium labeled | 87 | 37 |
| pIBI 31-BH5-2 | T7 | None | 208 | 100 |
| pIBI 31-BH5-2 | T7 | Allylamine labeled | 198 | 95 |
| pIBI 31BH-5-2 | T7 | Ethidium labeled | 3 | 1.4 |
| pBSII/HCV | T3 | None | 112 | 100 |
| pBSII/HCV | T3 | Allylamine labeled | 158 | >100 |
| pBSII/HCV | T3 | Ethidium labeled | 185 | >100 |
| pBSII/HCV | T7 | None | 125 | 100 |
| pBSII/HCV | T7 | Allylamine labeled | 154 | >100 |
| pBSII/HCV | T7 | Ethidium labeled | 62 | 50 |

These results indicate that the ethidium-modified oligo sequence is capable of specifically inhibiting transcription by the T7 polymerase from the T7 promotor region provided that the promoter region is not interrupted by the multiple cloning region and inserted DNA. Thus, the effect is dependent on the template DNA and is not merely the result of inhibition of the T7 polymerase by the ethidium groups.

Many obvious variations will be suggested to those of ordinary skill in the art in light of the above detailed description of the invention. All such variations are fully embraced by the scope and spirit of the present invention as set forth in the claims which follow.

What is claimed is:

1. An in vitro process for producing a specific nucleic acid, said process comprising the steps of:
   (a) providing a conjugate which is capable of producing a specific nucleic acid when present in a cell, said conjugate comprising a protein-nucleic acid construct, said construct comprising:
      (i) at least one promoter;
      (ii) at least one segment of said specific nucleic acid comprising a sequence coding for a protein; and
      (iii) an RNA polymerase;
   and (b) introducing said conjugate into a cell, thereby producing said specific nucleic acid.

2. The process of claim 1, wherein said protein-nucleic acid construct comprises a double-stranded nucleic acid.

3. The process of claim 1, wherein said sequence coding for a protein comprises a sequence for said RNA polymerase.

4. The process of claim 1, wherein said sequence coding for a protein comprises a sequence for said RNA polymerase wherein said sequence coding for a protein comprises a protein other than said RNA polymerase.

5. The process of claim 1, wherein said sequence coding for a protein comprises a sequence for said RNA polymerase and a sequence for a protein other than said RNA polymerase.

6. The process of claim 1, wherein said sequence coding for a protein comprises a sequence for a second RNA polymerase that is different from said RNA polymerase in said construct.

7. The process of claim 6, further comprising a second promoter for said second RNA polymerase.

8. The process of claim 7, further comprising a sequence for a protein, wherein said protein is transcribed from said second promoter.

9. An in vivo process for producing a specific nucleic acid, said process comprising the steps of:
   (a) providing a conjugate which is capable of producing a specific nucleic acid when present in a cell, said conjugate comprising a protein-nucleic acid construct, said construct comprising:
- (i) at least one promoter;
- (ii) at least one segment of said specific nucleic acid comprising a template for transcription; and
- (iii) an RNA polymerase;

and (b) introducing said conjugate into a cell, thereby producing said specific nucleic acid.

10. The process of claim 9, wherein said specific nucleic acid being produced comprises sense RNA or antisense RNA.

11. The process of claim 10, wherein said sense RNA codes for a protein.

12. The process of claim 11, wherein said protein coding sense RNA codes for said RNA polymerase.

13. The process of claim 11, wherein said protein coding sense RNA codes for a protein other than said RNA polymerase.

14. The process of claim 11, wherein said protein coding sense RNA codes for said RNA polymerase and a protein other than said RNA polymerase.

15. The process of claim 11, wherein said protein coding sense RNA comprises a sequence for a second RNA polymerase that is different from said RNA polymerase in said construct.

16. The process of claim 15, further comprising a second promoter for said second RNA polymerase.

17. The process of claim 16, further comprising a sequence for a protein, wherein said protein is transcribed from said second promoter.

18. An in vivo process for producing a specific nucleic acid, said process comprising the steps of:
- (a) providing a conjugate comprising a protein-nucleic acid construct, said conjugate being capable of producing a nucleic acid when present in a cell, wherein said construct comprises at least one complementary sequence to a primer present in said cell; and
- (b) introducing said conjugate into a cell, thereby producing said specific nucleic acid.

* * * * *